(12) United States Patent
Kleshinski et al.

(10) Patent No.: US 9,629,675 B2
(45) Date of Patent: Apr. 25, 2017

(54) TISSUE TREATMENT DEVICE AND RELATED METHODS

(71) Applicant: Confluent Medical Technologies, Inc., Fremont, CA (US)

(72) Inventors: Stephen J. Kleshinski, San Jose, CA (US); Christopher P. Cheng, Palo Alto, CA (US)

(73) Assignee: Confluent Medical Technologies, Inc., Fremont, CA (US)

( * ) Notice: Subject to any disclaimer, the term of this patent is extended or adjusted under 35 U.S.C. 154(b) by 701 days.

(21) Appl. No.: 13/656,601

(22) Filed: Oct. 19, 2012

(65) Prior Publication Data

US 2013/0103026 A1    Apr. 25, 2013

Related U.S. Application Data

(60) Provisional application No. 61/548,728, filed on Oct. 19, 2011.

(51) Int. Cl.
| | |
|---|---|
| *A61B 18/08* | (2006.01) |
| *A61B 18/14* | (2006.01) |
| *A61N 7/02* | (2006.01) |
| *A61B 18/00* | (2006.01) |
| *A61M 25/04* | (2006.01) |
| *A61M 25/00* | (2006.01) |
| *A61B 90/00* | (2016.01) |

(52) U.S. Cl.
CPC ........ *A61B 18/082* (2013.01); *A61B 18/1492* (2013.01); *A61B 90/39* (2016.02); *A61B 2018/00017* (2013.01); *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/00839* (2013.01); *A61B 2018/00875* (2013.01); *A61M 25/04* (2013.01); *A61M 2025/0087* (2013.01); *A61N 7/022* (2013.01)

(58) Field of Classification Search
CPC .......... A61B 18/18; A61B 17/22; A61M 1/00; A61M 31/00; A61M 25/00; A61M 25/10; A61D 7/00; H05K 7/00; A61F 7/123
USPC ........... 606/41; 604/28, 103.11, 508, 101.01, 604/523; 361/747; 600/585; 607/96
See application file for complete search history.

(56) References Cited

U.S. PATENT DOCUMENTS

| | | | |
|---|---|---|---|
| 5,021,045 A | 6/1991 | Buckberg et al. | |
| 5,431,649 A | 7/1995 | Mulier et al. | |
| 5,490,837 A * | 2/1996 | Blaeser et al. | ........... 604/103.11 |
| 5,588,960 A | 12/1996 | Edwards et al. | |

(Continued)

OTHER PUBLICATIONS

Draney et al.; Three-dimensional analysis of renal artery bending motion during respiration; J Endovasc Ther.; 12(3):380-6; Jun. 2005.

*Primary Examiner* — William Thomson
*Assistant Examiner* — Victor Shapiro
(74) *Attorney, Agent, or Firm* — Shay Glenn LLP

(57) ABSTRACT

A hypotube based deliver system is used to position one or more elements in position for treatment within the body. The elements may include electrodes, sensors or injection ports or even anchors. The hypotubes may have pre-set shapes or are plastically deformed prior to positioning as they exit a positioning device. There are methods of providing therapy using the hypotubes including mixed mode therapies are also described.

16 Claims, 26 Drawing Sheets

(56) References Cited

U.S. PATENT DOCUMENTS

| | | | |
|---|---|---|---|
| 5,913,842 A * | 6/1999 | Boyd et al. | 604/28 |
| 6,217,554 B1 | 4/2001 | Green | |
| 6,302,870 B1 | 10/2001 | Jacobsen et al. | |
| 7,056,286 B2 | 6/2006 | Ravenscroft et al. | |
| 8,021,351 B2 * | 9/2011 | Boldenow | A61B 17/22 604/523 |
| 8,077,470 B2 * | 12/2011 | Zhang et al. | 361/747 |
| 8,246,574 B2 * | 8/2012 | Jacobs | A61M 25/0045 600/585 |
| 8,398,672 B2 | 3/2013 | Kleshinski et al. | |
| 8,409,239 B2 | 4/2013 | Kleshinski et al. | |
| 8,663,190 B2 | 3/2014 | Fischell et al. | |
| 2001/0031941 A1 | 10/2001 | Edwards et al. | |
| 2001/0041862 A1 * | 11/2001 | Glickman | A61M 25/1011 604/101.01 |
| 2002/0026150 A1 | 2/2002 | Palasis et al. | |
| 2003/0018318 A1 | 1/2003 | Melsky | |
| 2005/0131451 A1 | 6/2005 | Kleshinski et al. | |
| 2007/0129720 A1 * | 6/2007 | Demarais et al. | 606/41 |
| 2007/0135875 A1 * | 6/2007 | Demarais | A61F 7/123 607/96 |
| 2008/0213331 A1 | 9/2008 | Gelfand et al. | |
| 2009/0131886 A1 | 5/2009 | Liu et al. | |
| 2010/0168739 A1 * | 7/2010 | Wu et al. | 606/41 |
| 2011/0125131 A1 * | 5/2011 | Chang | A61M 25/0084 604/508 |
| 2011/0313417 A1 | 12/2011 | De La Rama et al. | |
| 2012/0059286 A1 | 3/2012 | Hastings et al. | |
| 2012/0101413 A1 | 4/2012 | Beetel et al. | |
| 2012/0116392 A1 | 5/2012 | Willard | |
| 2012/0123406 A1 | 5/2012 | Edmunds et al. | |
| 2013/0053792 A1 | 2/2013 | Fischell et al. | |
| 2013/0053821 A1 | 2/2013 | Fischell et al. | |
| 2013/0053822 A1 | 2/2013 | Fischell et al. | |

\* cited by examiner

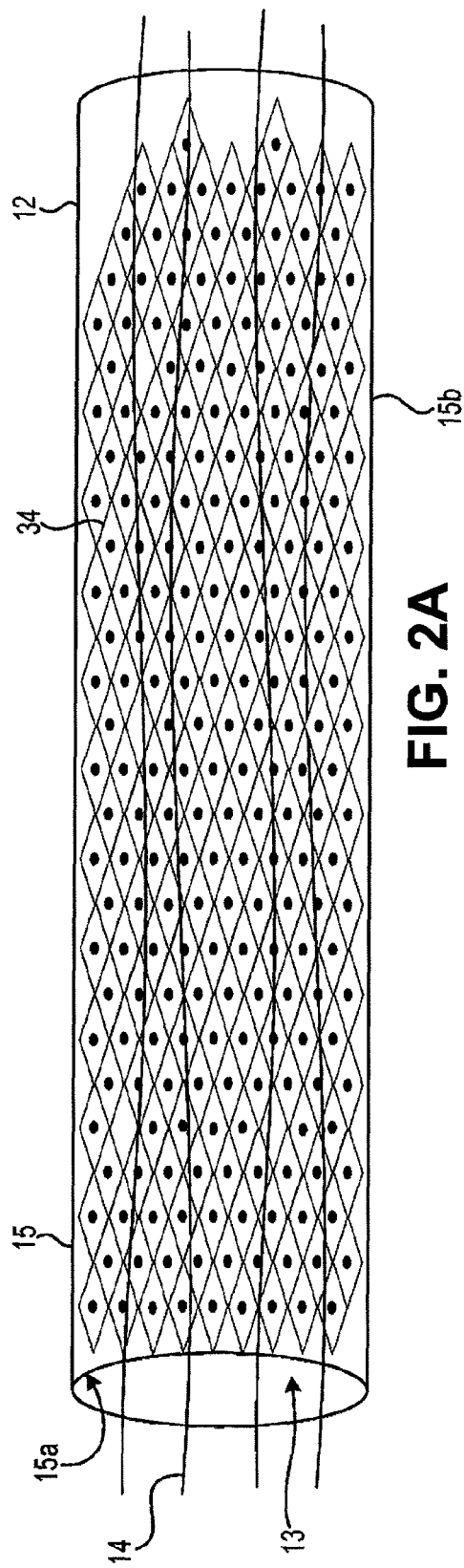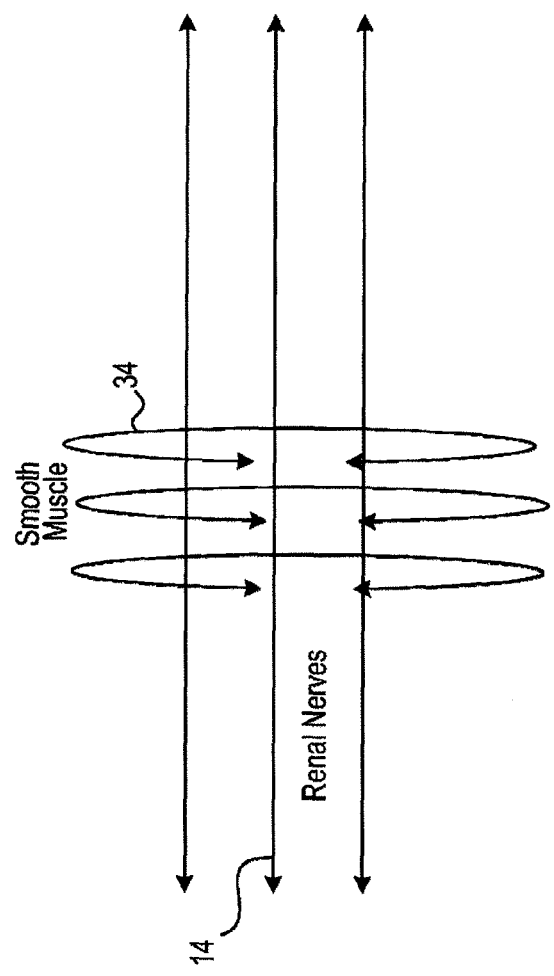
FIG. 2A
FIG. 2B

FIG. 9A  FIG. 9B  FIG. 9C

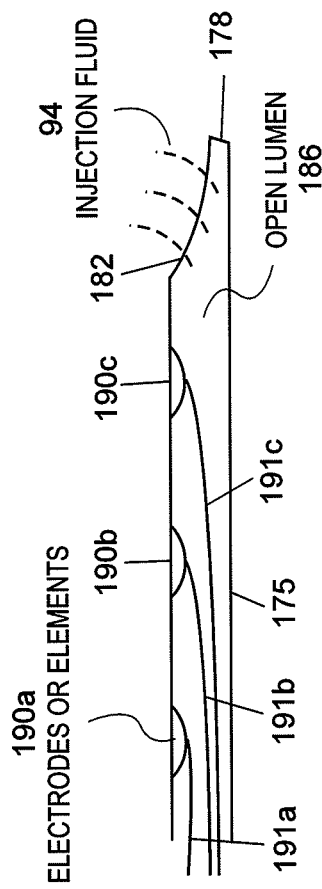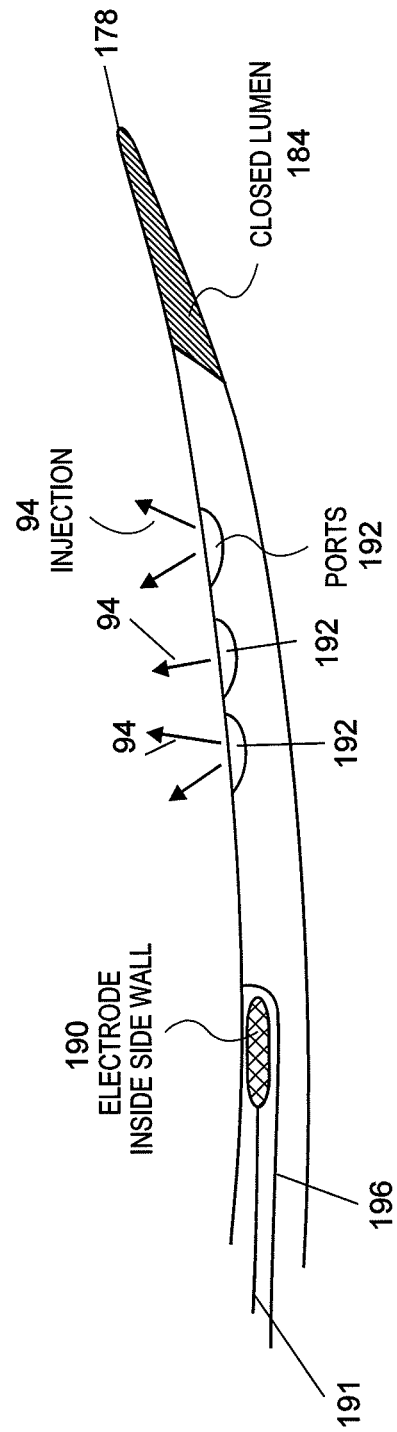

TISSUE TREATMENT DEVICE AND RELATED METHODS

CROSS REFERENCE TO RELATED APPLICATION

This application claims the priority of U.S. Provisional Patent Application No. 61/548,728, filed on Oct. 19, 2011, titled "TISSUE ABLATION DEVICE," which is herein incorporated by reference in its entirety.

STATEMENT AS TO FEDERALLY SPONSORED RESEARCH

This invention was not made with federally sponsored research.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates to methods and devices for accessing and placement of treatment devices within the human or animal body.

BACKGROUND

Tissue ablation refers to the destruction of tissue. The most ancient form of tissue ablation is surgery, whereby pathological tissues are physically removed from the body.

Over the last 40 to 50 years, considerable progress has been made toward ablative techniques that are both minimally invasive i.e., do not require open surgery, and affect very localized tissue areas. Examples include Radio Frequency (RF), cryo-ablation, and laser ablation of tumors that can develop anywhere in the body; RF, cryo-ablation, and laser ablation of blood vessels; RF and laser ablation of various cardiac structures, especially in the left atrium of the heart for the treatment of atrial fibrillation and other conduction disorders. Most recently it has been demonstrated that ablation of the nerves supplying the renal arteries can lead to dramatic reductions in blood pressure in patient populations unresponsive to drug based blood pressure controls.

One significant problem associated with current ablative technologies is that they still destroy whole volumes of tissue without regard to their cellular content. This can lead to other types of dysfunction that are not intended consequences of the therapy. An example of this is ablation of the tissues surrounding the openings of the pulmonary veins into the left atrium in the treatment of atrial fibrillation. The thermal heat of RF ablation, or the freezing of tissue in cryo-ablation destroys not only the neurons that the clinician wants to destroy, but also a volume of otherwise useful muscular tissue of the atrium. The same is true for the new technique of renal ablation wherein the entire wall of the renal artery is thermally coagulated in certain areas in order to destroy the nerves located mainly in the outer covering of the artery known as the adventitia. This may leave the artery less compliant than it would be otherwise, and also cause areas of stenosis that may restrict normal blood flow to the kidneys. Another unwanted side effect of many of the ablative technologies is that they cause significant pain.

What is needed are improved therapy delivery systems and methods of improved treatment that overcome the short comings of the previous systems.

SUMMARY OF THE DISCLOSURE

In one aspect, there is provided a hypotube based therapy device having a positioning device disposed within and moveable relative to a delivery catheter lumen to extend beyond the catheter distal end portion. The positioning device comprising a plurality of hollow, outwardly biased legs. A hypotube is disposed within and moveable relative to a distal end of one of the plurality of hollow legs. The hypotube has at least one element used for performing an action when the element is positioned away from the hollow leg. Still further, the hypotube has a pre-set shape such that when the hypotube is advanced through the lumen of an outwardly biased leg the element on the hypotube is positioned to perform the action. In additional aspect, in use during or after performing the action, a pharmacological agent is disposed within the lumen of the pre-shaped hypotube. Still further, in use during or after performing the action, a liquid ablation agent is disposed within the lumen of the pre-shaped hypotube. In another aspect, in use during or after performing the action, a therapeutic agent is disposed within the lumen of the pre-shaped hypotube related to treatment of a disorder in a treatment site within a therapeutic proximity to the element.

In another aspect of the hypotube based therapy device, the length of the delivery catheter is sufficient to place the catheter distal end within a renal artery of a patient and the proximal end outside of the patient.

In still another aspect, the therapy device also includes a handle at the catheter proximal end having a slider to cock a spring loaded mechanism connected to the pre-shaped hypotube. Optionally or additionally, the handle at the catheter proximal end having a button or trigger to release a mechanism connected to the pre-shaped hypotube to automatically drive the hypotube from the hollow leg, or a handle at the catheter proximal end having an injection port in fluid communication with a lumen of the hypotube and an opening in the hypotube distal portion.

In another aspect of the therapy device, a lumen of the hypotube is opened to the distal most end of the hypotube, alone or in combination with an opening in the sidewall of the hypotube and in communication with the hypotube lumen. Optionally, a distal most opening of one or more the hypotube lumens in a delivery device is closed off. In still other alternatives, a plug is inserted into the lumen of each hollow outwardly biased leg to close off the lumen. The plug may also include a shaped surface configured to direct a hypotube advancing within the lumen of a hollow leg out of an opening formed in a sidewall of the hollow leg. Optionally, the plug or other shaped surface presented in the hollow leg lumen adjacent an opening or presented to the lumen of the hollow leg, the surface configured to plastically deform a hypotube advancing within the lumen of a hollow leg to form the advanced hypotube into a shape for performing an action using the element on the hypotube. In another aspect, there may be a cap placed over the distal most end of the hollow leg to close off the lumen of the hollow leg.

In still another aspect, the hypotube based therapy device has at least one element that is positioned at least partially along the hypotube on an outer or inner surface or in or within the hypotube lumen. In some embodiments, the hypotube elements are positioned at least partially along an outer radial portion of a hypotube or at least partially along an inner radial portion of the hypotube. The hypotube may be preshaped or shape set prior to use or plastically deformed while being introduced into the body or as the hypotube exits the hollow leg into which it is disposed. In one particular aspect, there is an additional step for: imposing a curvature on the hypotube related to the pre-determined trajectory prior to the advancing the hypotube step. The step of imposing a curvature on the hypotube related to the pre-determined trajectory during the advancing the hypotube step. Optionally, there may be provided the step of plastically deforming the hypotube according to the pre-determined trajectory as the hypotube exits a lumen of the positioning device.

In another aspect, there is a handle at the catheter proximal end having a button used to control the operation of the element to perform the operation. In still other aspects the handle or trigger or additional systems used in conjunction with the hypotube are selected based on the type of element used on the one or more hypotubes. The hypotube elements include one or more of, in any combination, a treatment electrode, a sensing electrode, a sensing element, an transducer, a piezoelectric element, a heating element, a nozzle for delivering a fluid via the hypotube, and a port for delivering a fluid via the hypotube. In other aspect, a hypotube element may include a first injection port at a first spacing from the distal most end of the hypotube and a second injection port at a second spacing from the distal most end of the hypotube. In one embodiment, first spacing is 110°-140° and the second spacing is 40°-70°. In another embodiment, the first spacing is three to four times the hypotube diameter and the second spacing is from 0.003 inches to 0.010 inches. In another aspect, each of the plurality of hollow, outwardly biased legs further comprising: an opening in a sidewall of the leg positioned to permit movement of the hypotube within the leg lumen out of the opening. Further still, there is a support portion on the leg distal to the opening in the sidewall and proximal to the distal most end of the leg. In one embodiment, the support portion is a cap inserted onto the hollow leg. In another embodiment, there is, on a hollow leg or a hypotube a marker used to identify the type of leg or hypotube using a medical imaging system (e.g., x-ray) in one configuration, the marker is positioned on the outwardly biased leg identifiable using medical imaging used to indicate the type of element on the hypotube disposed within the hollow leg. The marker is positioned on the distal portion of the outwardly biased leg distal to a position where the hypotube disposed within the hollow leg exits the hollow leg lumen.

In an additional aspect, a hypotube has a length and a curvature sufficient to place the at least one element in a position to provide a therapy using the element. Additionally or alternatively, a hypotube includes a distal portion shaped for penetrating through a structure adjacent to the leg upon advancement through the opening in the hollow leg. In another aspect, a distal portion of the hypotube having a shape for securing the hypotube into a structure after the hypotube is extended beyond the hollow leg lumen. Optionally, the radius of curvature of a hypotube distal portion is selected to position the distal most portion of the hypotube into a position relative to the opening in the leg and with the active element in a position for performing an action using the therapy device. In some embodiments, there is a pre-shaped hypotube in each one of the plurality of hollow legs. In one aspect, each hypo tube has an element, in another aspect alternate hypo tubes contain only anchors. In still additional versions, there is also a mechanism on the proximal end of the catheter coupled to each of the pre-shaped hypotubes for moving each of the pre-shaped hypotubes relative to the hollow legs. The mechanism is optionally configured to simultaneously move all of the pre-shaped hypotubes relative to the positioning device to position all of the elements away from the hollow leg to perform the action.

In one embodiment, the elements provided by the hypo tubes enable a mixed mode therapy. In still other aspects, a portion of the hypo tubes are used to anchor. Still further, the first portion of the hypotubes have an element selected for performing an ablation action and a second portion of the hypotubes have an element selected for detecting, monitoring or recording the effectiveness or progress of the ablation action performed by the first portion of the hypotubes.

In one embodiment, there is provided a method for performing a procedure in the body by advancing a catheter within a lumen of the body to a position suited to performing the procedure. Thereafter, there is a step of advancing a delivery system positioning device through the catheter to place at least one opening in a positioning device of the delivery system relative to a treatment location based on a pre-determined trajectory of a hypotube disposed within a lumen of the positioning device. Next, advancing the hypo tube through the opening until an element on the distal portion of the hypotube is positioned to perform a procedure in proximity to the treatment location. Afterwards, there is one or more steps of performing a procedure in the treatment location using the element.

In one aspect, performing a procedure step occurs outside of the lumen of the body. Optionally, the performing a procedure step treats a neural treatment target unrelated to the lumen. In some methods, the performing a procedure step comprises a denervation procedure.

The method of the performing a procedure step may include for example, delivering energy using the element; injecting a fluid using the hypotube; monitoring the progress or effectiveness of the performing a procedure step using an element on a hypotube; or monitoring the progress or effectiveness of the performing a procedure step using an element on a hypotube that is also being used for the performing a procedure step, each alone or in any combination.

In additional optional steps, there may be a step of continuing to advance the hypotube to anchor the element in a position for performing the procedure. Additionally or optionally, when anchored the distal end of the hypotube engages with the outer wall of the lumen or when anchored the distal end of the hypotube engages with a tissue in the vicinity to the location for the procedure.

In one aspect, the lumen is a renal artery and the procedure is a denervation procedure. In still further alternatives of the method, the performing a procedure in the treatment location includes delivering a fluid to the treatment location, delivering energy to the treatment location, ablating tissue in an organ, portion of the body or a portion of the nervous system or the vasculature, or treating a tumor alone or in any combination of the above.

In still another aspect, performing a procedure in proximity to the treatment location is a position related to the therapeutic range of the energy delivered by the element. Still further, the hypo tube element is positioned to perform a procedure in proximity to the treatment location is a position related to the dispersion of a fluid delivered by the element.

In still another alternative aspect, there is provided a method of performing a therapy within a patient by positioning a delivery catheter within the patient at a treatment location. Next is a step of expanding outwardly biased hollow legs of a positioning device into engagement in proximity to the treatment location. There is a step of advancing hypotubes out of the hollow legs so as to position an element carried by the hypotube within a therapeutic range of a target in the treatment location. Then, there is the step of performing an action in furtherance of the therapy using the element. In one alternative, the action in furtherance of the therapy is ablating at least a portion of the target. In another alternative, the action in furtherance of the therapy is monitoring, measuring or recording the effectiveness or progress of the ablating step. In any of the above described embodiments, the target is one or more of a nerve, a ligament, a tumor, a vessel, a sphincter, an organ or a muscle. In other aspect, after the advancing step the hypotubes have exited the hollow legs via the distal most end of the hollow leg or via an opening in a sidewall of the hollow leg.

In any of the above embodiments, each one of the hypotubes in the delivery system may include one or more injection ports either through the distal most opening of the hypotube lumen or via a sidewall. The hypotubes in such a configuration may be considered a plurality of fluid delivery structures (FDS) or hypotube delivery element that can be deployed individually or simultaneously, as desired. In additional or alternative embodiments, one or more hypotubes or FDS can be utilized for delivery of one or more of a fluid, a gas, an electrical element or one or more therapeutic agents, in any combination by adjusting the element or elements on one or more hypotubes. In still further alternative, one or more of the FDS can be deployed to predetermined depths within adjacent structures, therapeutic targets, or other anatomical locations. In still further embodiments, one or more of the FDS can be directed to specific locations within the body. In one specific embodiment, the therapeutic target for one or more of the FDS is an abluminal surface of renal artery adventitia.

In still in additional aspects, the size, shape and material selection of the hollow legs of the positioning device may be selected to provide a backing force for driving the hypotubes or FDS. In still further embodiments, the backing force provided by the hollow legs can be tailored to the therapeutic application by strengthening, or weakening the backing force. In still further aspects, the backing force may be used to ensure proper apposition of any sidewall or distal end opening to ensure proper contact between the tip of a hypotube and the tissue. In one particular embodiment, the hollow legs of the delivery device are made from nitinol, the backing force may be provided using shape set or shape memory properties of the material tailored to the therapeutic application.

Since the hollow legs are independent of the delivery catheter, the legs can accommodate variations in luminal diameter by adjustments in size, outward force or other characteristics as desired by the desired therapeutic outcome or anatomical site.

The choice of drive mechanisms such as a spring loaded or other conventional type of actuation force for the movement of the hypotubes out of the legs and through the adjacent tissue or target site can be tailored for various anatomic structural differences, type of tissue or other anatomical or physiological considerations (i.e., presence of bone, ligaments, wall thickness, plaque, scar tissue, proximity to critical structures to be avoided, proximity to additional structures to be treated, the therapeutic range of one or more elements or treatment modality, and the like).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A and 2B illustrate sympathetic innervation of the renal artery.

FIG. 9A is an enlarged side view of a distal portion of a hollow leg of FIG. 6A showing a hypotube tip just exiting an opening in the hollow leg sidewall.

FIG. 9B is a top view of the distal portion of a hollow leg and end cap without a hypotube to inside the lumen of the hollow leg through an opening in the hollow leg sidewall.

FIG. 9C is a top view of an alternative distal hollow leg portion of a hollow leg without a hypotube inside the lumen of the hollow leg through an opening in a sidewall of the hollow leg and a filled lumen at the furthest distal portion of the hollow leg.

FIG. 12D is a cross section view similar to the embodiment of FIG. 12C with injection of a therapeutic fluid through the lumen at the distal most end and three sidewall elements each having separate connection lines to the proximal end of the hypotube.

FIG. 12E is a section view of an alternative hypotube embodiment with a closed off distal tip and having three injection port elements in communication with the hypotube lumen and a separate lumen or cavity containing an additional element within the sidewall of the hypotube.

FIGS. 14A, B and C also illustrate a coordinate system used to describe elements locations.

DETAILED DESCRIPTION

Figure 1:
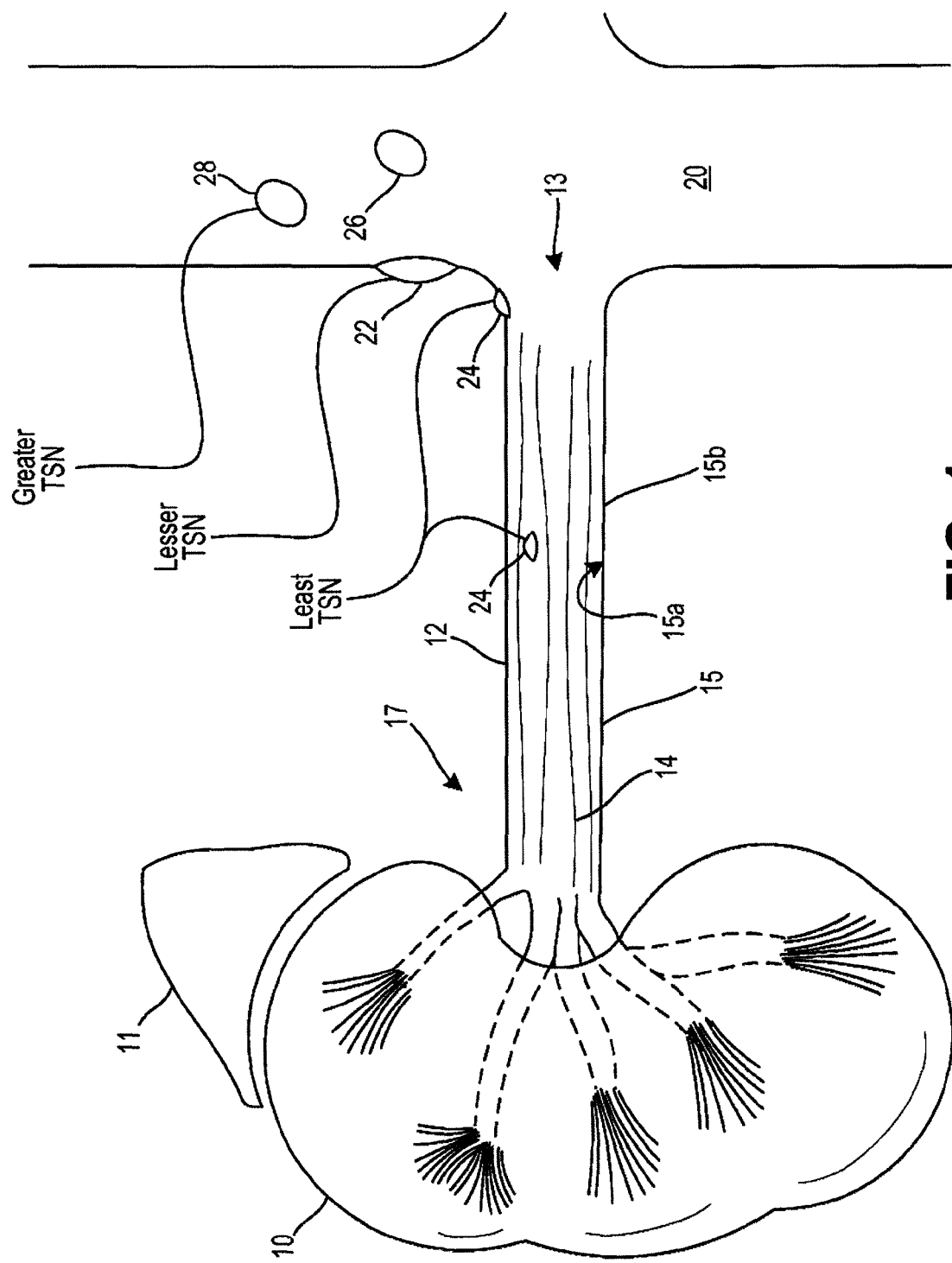
FIG. 1 is an illustration of a right kidney and renal vasculature including a renal artery branching laterally from the abdominal aorta.

Various embodiments of the disclosure are directed to apparatuses and methods for renal denervation for treating hypertension. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the disclosure. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
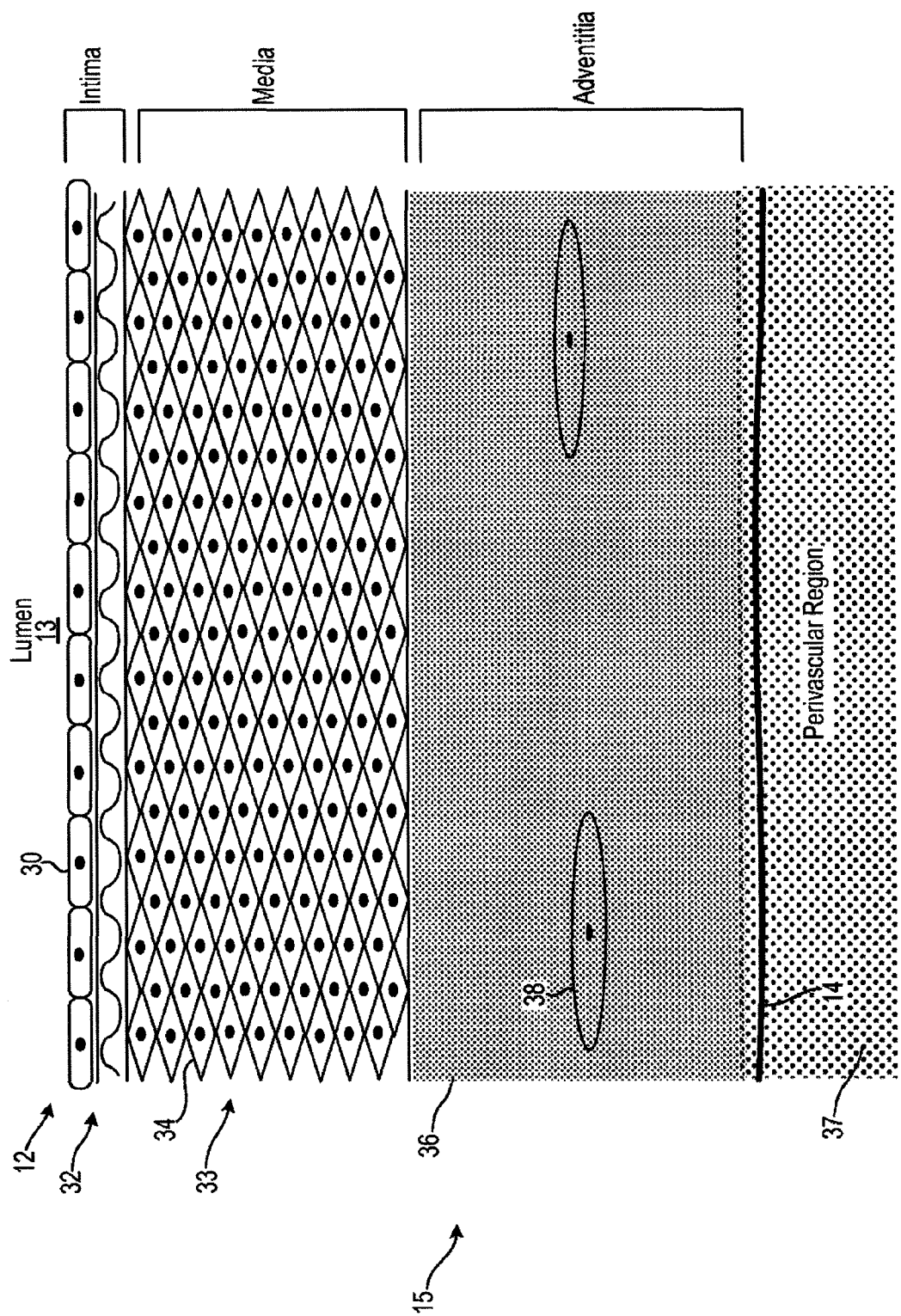
FIG. 3A illustrates various tissue layers of the wall of the renal artery.

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to enervate the renal artery smooth muscle 34.

Embodiments of the disclosure may be implemented to provide varying degrees of denervation therapy to innervated renal vasculature. For example, embodiments of the disclosure may provide for control of the extent and relative permanency of renal nerve impulse transmission interruption achieved by denervation therapy delivered using a treatment apparatus of the disclosure. The extent and relative permanency of renal nerve injury may be tailored to achieve a desired reduction in sympathetic nerve activity (including a partial or complete block) and to achieve a desired degree of permanency (including temporary or irreversible injury).

Figure 3B:
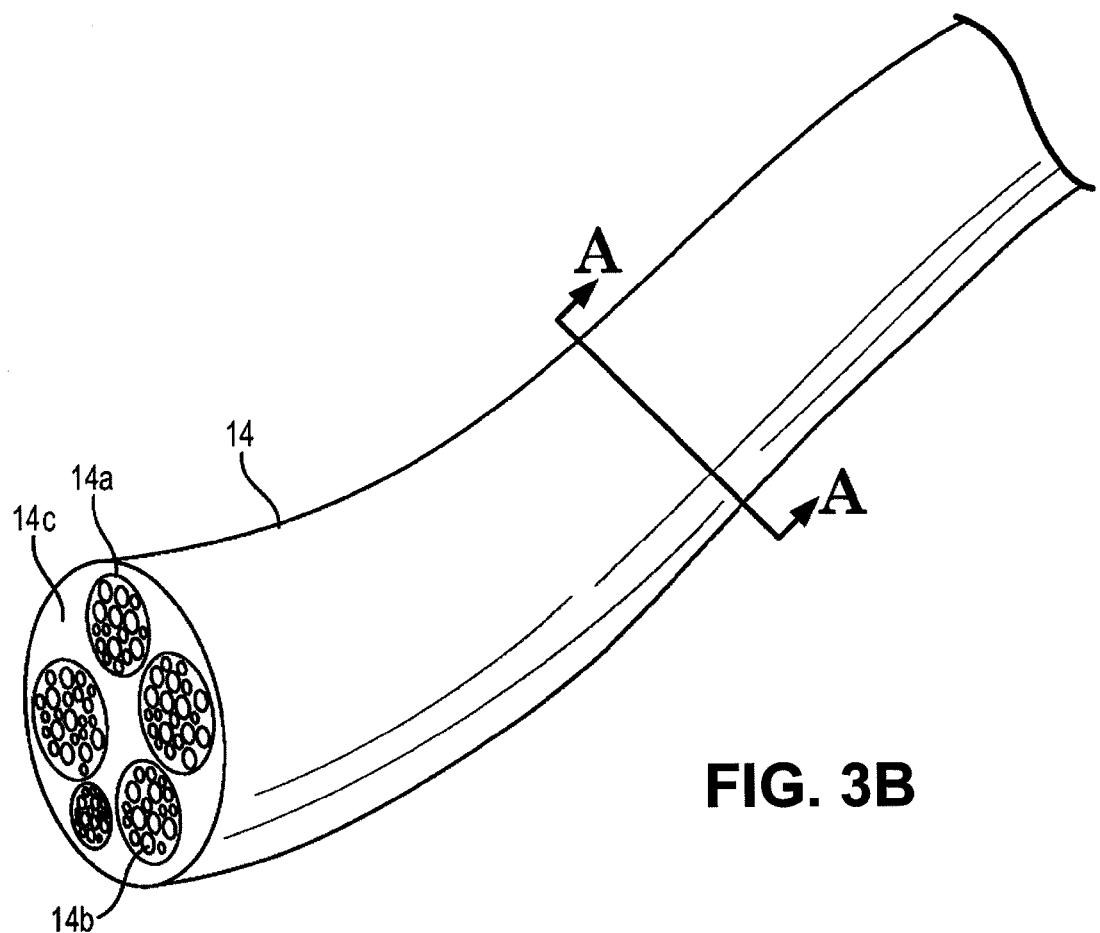
FIGS. 3B and 3C illustrate a portion of a renal nerve.
Figure 3C:
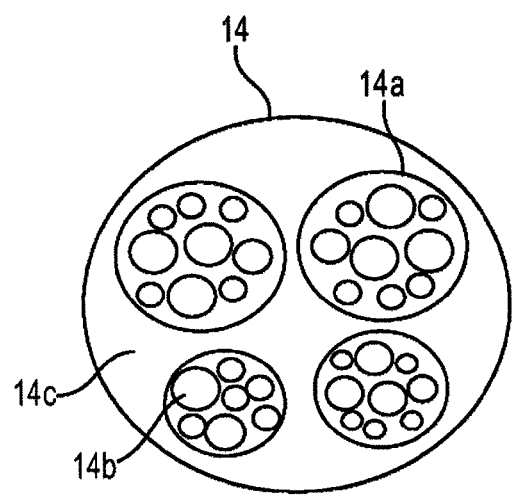

Returning to FIGS. 3B and 3C, the portion of the renal nerve 14 shown in FIGS. 3B and 3C includes bundles 14a of nerve fibers 14b each comprising axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a. In particular, the endoneurium, also referred to as the endoneurium tube or tubule, is a layer of delicate connective tissue that encloses the myelin sheath of a nerve fiber 14b within a fasciculus.

Major components of a neuron include the soma, which is the central part of the neuron that includes the nucleus, cellular extensions called dendrites, and axons, which are cable-like projections that carry nerve signals. The axon terminal contains synapses, which are specialized structures where neurotransmitter chemicals are released in order to communicate with target tissues. The axons of many neurons of the peripheral nervous system are sheathed in myelin, which is formed by a type of glial cell known as Schwann cells. The myelinating Schwann cells are wrapped around the axon, leaving the axolemma relatively uncovered at regularly spaced nodes, called nodes of Ranvier. Myelination of axons enables an especially rapid mode of electrical impulse propagation called saltation.

In some embodiments, a treatment apparatus of the disclosure may utilize the shape, length, or curvature of one or more hypotubes to deliver denervation therapy that causes transient and reversible injury to renal nerve fibers 14b. In other embodiments, a hypotube based treatment apparatus of the disclosure may be implemented to deliver denervation therapy that causes more severe injury to renal nerve fibers 14b, which may be reversible if the therapy is terminated in a timely manner. In additional embodiments, a treatment apparatus of the disclosure may be implemented to deliver denervation therapy that causes severe and irreversible injury to renal nerve fibers 14b, resulting in permanent cessation of renal sympathetic nerve activity. For example, a treatment apparatus may utilize one or more hypotube delivered elements to deliver or perform a denervation therapy that disrupts nerve fiber morphology to a degree sufficient to physically separate the endoneurium tube of the nerve fiber 14b, which can prevent regeneration and re-innervation processes.

By way of example, and in accordance with Seddon's classification as is known in the art, a treatment apparatus of the disclosure may utilize one or more hypotube delivered elements to deliver a denervation therapy that interrupts conduction of nerve impulses along the renal nerve fibers 14b by imparting damage to the renal nerve fibers 14b consistent with neruapraxia. Neurapraxia describes nerve damage in which there is no disruption of the nerve fiber 14b or its sheath. In this case, there is an interruption in conduction of the nerve impulse down the nerve fiber, with recovery taking place within hours to months without true regeneration, as Wallerian degeneration does not occur. Wallerian degeneration refers to a process in which the part of the axon separated from the neuron's cell nucleus degenerates. This process is also known as anterograde degeneration. Neurapraxia is the mildest form of nerve injury that may be imparted to renal nerve fibers 14b by use of a hypotube based treatment apparatus according to embodiments of the disclosure.

An embodiment of a hypotube based treatment apparatus may be implemented using one or more elements to interrupt conduction of nerve impulses along the renal nerve fibers 14b by imparting damage to the renal nerve fibers consistent with axonotmesis. Axonotmesis involves loss of the relative continuity of the axon of a nerve fiber and its covering of myelin, but preservation of the connective tissue framework of the nerve fiber. In this case, the encapsulating support tissue 14c of the nerve fiber 14b are preserved. Because axonal continuity is lost, Wallerian degeneration occurs. Recovery from axonotmesis occurs only through regeneration of the axons, a process requiring time on the order of several weeks or months. Electrically, the nerve fiber 14b shows rapid and complete degeneration. Regeneration and re-innervation may occur as long as the endoneural tubes are intact.

An embodiment of a hypotube based treatment apparatus as described herein may be implemented using one or more hypotube delivered elements to interrupt conduction of nerve impulses along the renal nerve fibers 14b by imparting damage to the renal nerve fibers 14b consistent with neurotmesis. Neurotmesis, according to Seddon's classification, is the most serious nerve injury in the scheme. In this type of injury, both the nerve fiber 14b and the nerve sheath are disrupted. While partial recovery may occur, complete recovery is not possible. Neurotmesis involves loss of continuity of the axon and the encapsulating connective tissue 14c, resulting in a complete loss of autonomic function, in the case of renal nerve fibers 14b. If the nerve fiber 14b has been completely divided, axonal regeneration causes a neuroma to form in the proximal stump.

A more stratified classification of neurotmesis nerve damage may be found by reference to the Sunderland System as is known in the art. The Sunderland System defines five degrees of nerve damage, the first two of which correspond closely with neurapraxia and axonotmesis of Seddon's classification. The latter three Sunderland System classifications describe different levels of neurotmesis nerve damage.

The first and second degrees of nerve injury in the Sunderland system are analogous to Seddon's neurapraxia and axonotmesis, respectively. Third degree nerve injury, according to the Sunderland System, involves disruption of the endoneurium, with the epineurium and perineurium remaining intact. Recovery may range from poor to complete depending on the degree of intrafascicular fibrosis. A fourth degree nerve injury involves interruption of all neural and supporting elements, with the epineurium remaining intact. The nerve is usually enlarged. Fifth degree nerve injury involves complete transection of the nerve fiber 14b with loss of continuity.

Aspects of the hypotube based therapeutic system described herein can, according to its various embodiments, provide a more effective, accurate, and controlled way to provide treatment to a variety of tissues while minimizing collateral damage to surrounding tissues. One key feature of achieving such a variety of therapy goals stems from the adaptability of the hypotube to position one or more elements to produce a therapeutic effect or treatment at an intended therapeutic site.

In one aspect of a desired clinical use, an ablation fluid is injected using a hypotube injection port positioned at a therapeutic site within the body. Examples of ablation fluids include alcohol, %6 Phenol, Botulinum toxin, other neurolytic compounds and the like.

In one aspect of one possible proposed clinical use, an embodiment of the capability of the invention is to block the sympathetic activity of the renal nerve of the kidney by controlled local delivery via one or more hypotube ports of a nerve-blocking agent with the goal of improving the patient's renal and cardiac function. Elements of the invention are useful for blocking nerves for the purpose other than treating cardiorenal disease and can be applied in other anatomic locations by adapting the element and hypotube curvature, length and other aspects to reach a therapeutic target or desired treatment site.

A nerve blocking agent is a drug that reduces or blocks conduction of signals by renal nerves. The nerve blocking agents used can be selected from different groups including (1) local anesthetics, (2) ketamine (a well known sedative with nerve blocking properties), (3) tricyclic antidepressants such as amitriptyline, (4) neurotoxins such as tetrodotoxin and saxitoxin or (5) any other class or type of agent that transiently or permanently, partially or completely alters nerve conduction. The terms nerve blocking agent and nerve blocking drug are interchangeable.

Cardiorenal disease is defined as a condition, chronic or acute, that involves both the heart and the kidney. Examples of cardiorenal diseases are hypertension and CHF. Cardiorenal diseases are characterized by the elevated activity of the renal nerve.

As used herein, the renal nerve is defined as any individual nerve or plexus of nerves and ganglia that conducts a nerve signal to and/or from the kidney and is anatomically located on the surface of the renal artery, parts of aorta where the renal artery branches from the aorta and/or on branches of the renal artery. The renal nerve generally enters the kidney in the area of the hilum of the kidney, but may enter in any location where a renal artery or branch of the renal artery enters the kidney.

Periarterial space is defined as the space immediately surrounding the renal arteries, renal veins and their branches between the aorta and the hilum of the kidney. The renal fat pad is defined as the adipose tissue or fat that fills the periarterial space and surrounds the renal artery, renal vein, renal nerves and the kidney itself. The renal fascia is the layer of connective tissue that surrounds, envelopes and contains the renal artery, renal vein, renal fatpad and the kidney itself.

Figure 4:
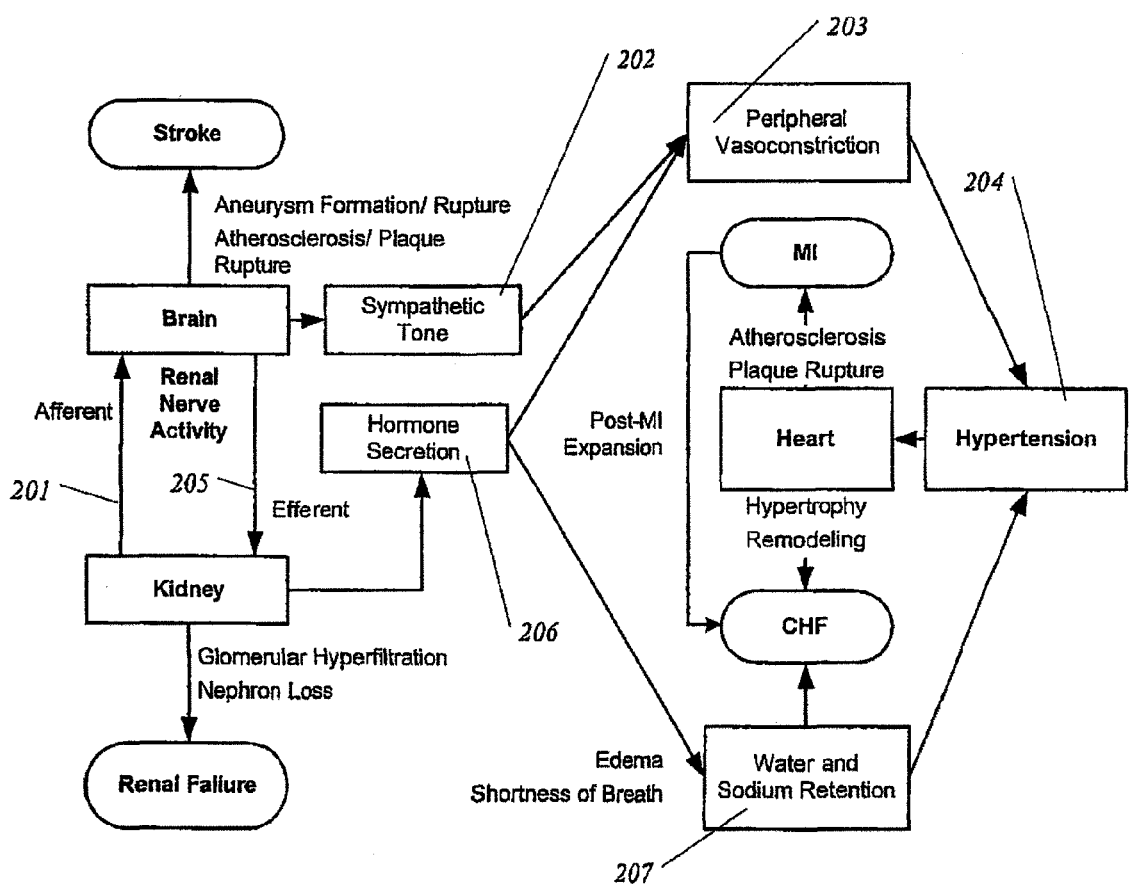
FIG. 4 illustrates the physiologic mechanisms of renal nerve modulation.

FIG. 4 illustrates the role of renal nerve activity in the progression of chronic cardiac and renal diseases. Increased renal afferent (from the kidney to the brain) nerve activity 201 results in the increased systemic sympathetic tone 202 and vasoconstriction (narrowing) 203 of blood vessels. Increased resistance of blood vessels results in hypertension 204. Hypertension is a major contributor to the progression of chronic heart failure and renal failure as well as the acute events such as strokes and myocardial infarcts. Increased renal efferent (from the brain to the kidney) nerve activity 205 results in further increased afferent renal nerve activity, secretion of the renal hormone renin 206, and reduction of renal blood flow and the decreased water and sodium excretion by the kidney. Renin contributes to systemic vasoconstriction of blood vessels 203. In combination these renal factors result in fluid retention 207 and increased workload of the heart thus contributing to the further deterioration of the patient. It should be clear from the FIG. 4 that moderation of renal nerve activity will benefit patients with heart, kidney and circulatory system (cardiorenal) diseases.

Figure 5:
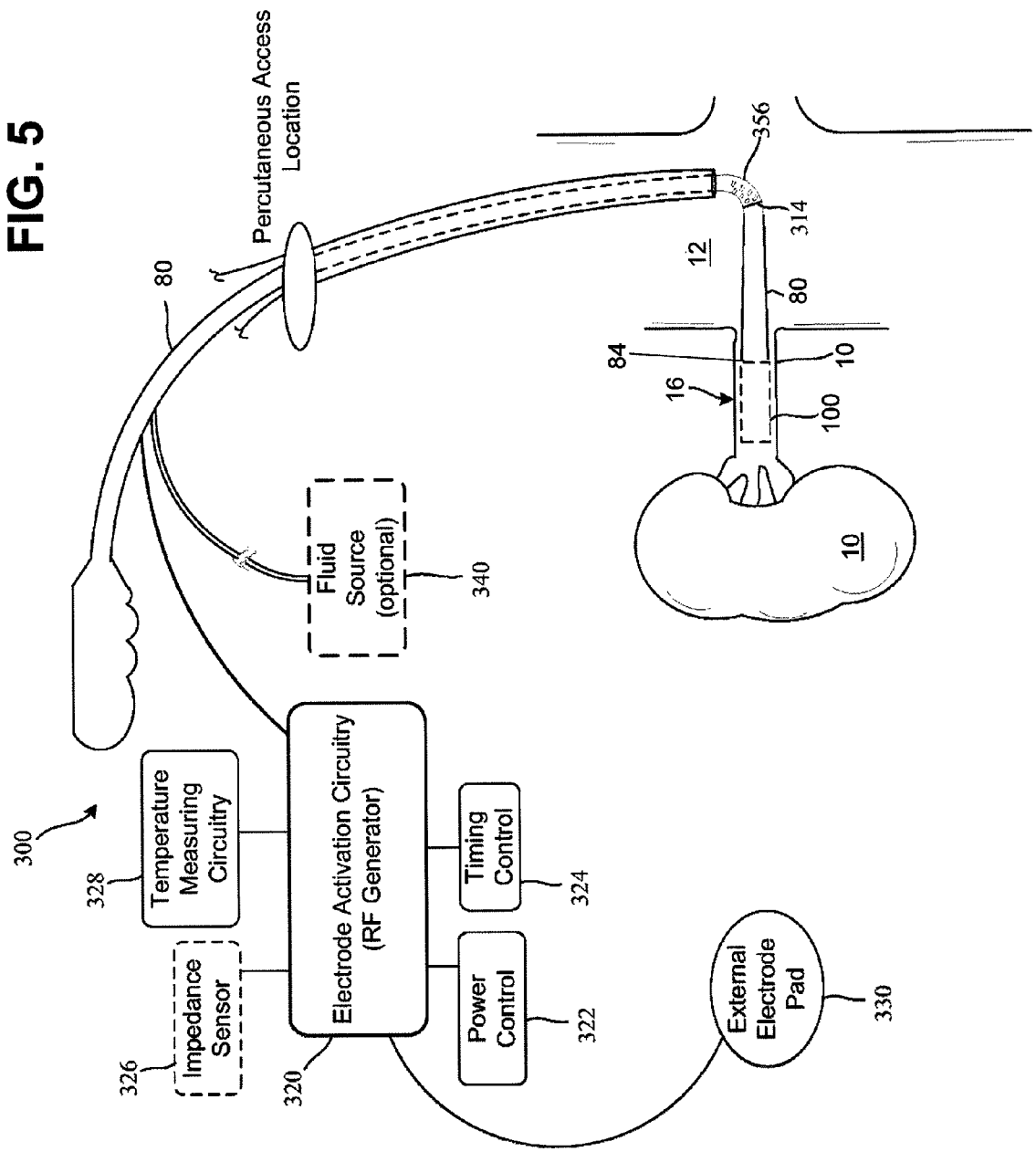
FIG. 5 shows a representative RF renal therapy apparatus in accordance with various embodiments of the disclosure.
Figure 6A:
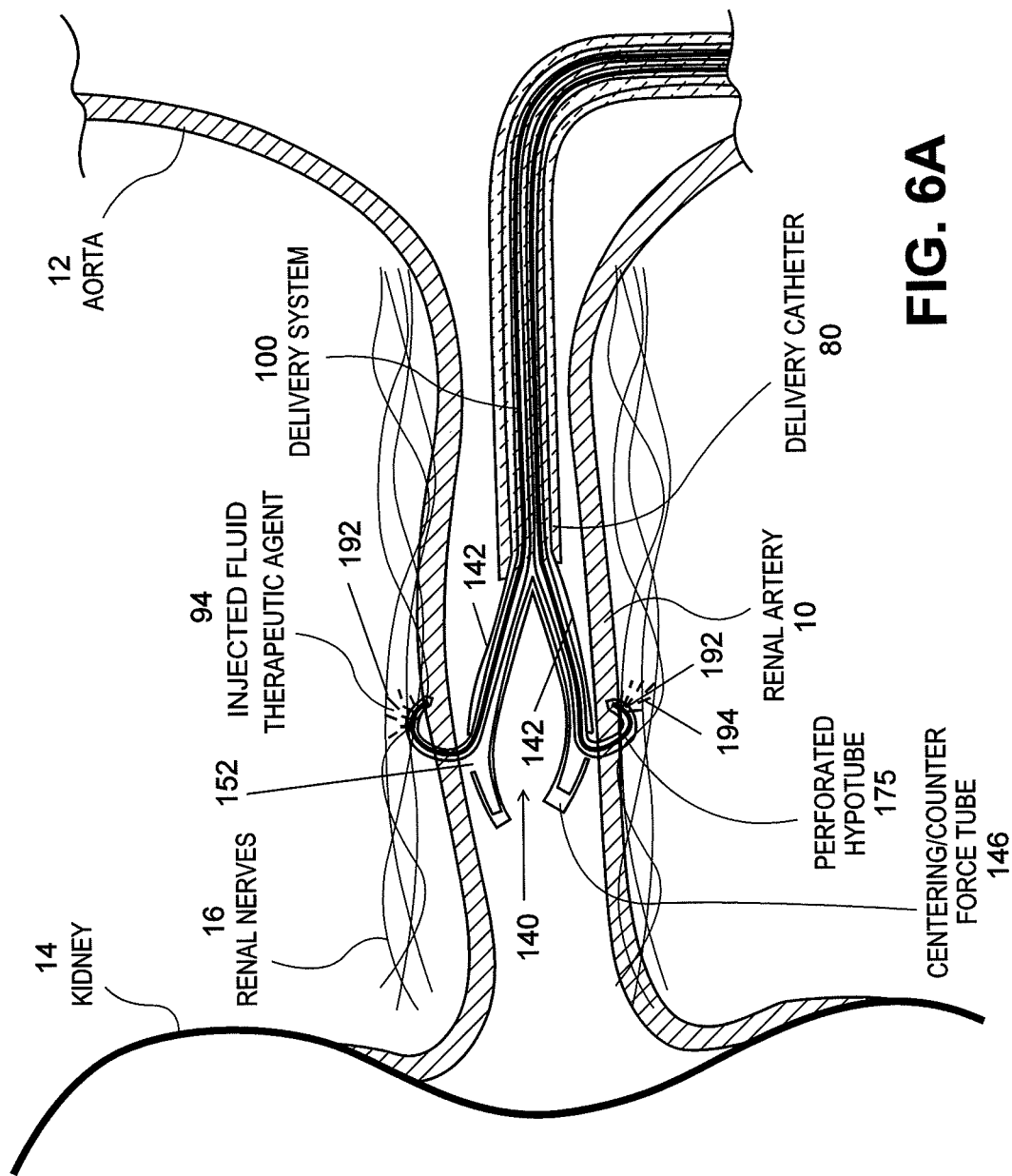
FIG. 6A is a section view of an embodiment of the therapy device within the renal artery and performing an action outside of the renal artery.

FIG. 5 shows a representative RF renal therapy apparatus 300 in accordance with various embodiments of the disclosure. FIG. 6A is a section view of an embodiment of the therapy device within the renal artery and performing an action outside of the renal artery.

FIG. 6A illustrates the delivery catheter 80 having a distal end 84 positioned within a lumen adjacent to a target site. Here the lumen is the renal artery 10 and the target site is nerves 16. The position of the distal end 84 is selected so that when the delivery system 100 is advanced beyond the distal end 84 the hollow legs 142 of the positioning device 140 are in a predetermined position. The predetermined position or injection location is selected based on a number of factors in order that the delivery of the hypotubes via the lumens 154 results in the placement of hypotube borne elements into the desired location adjacent a target or targets to achieve a therapeutic result as described herein. As shown in FIG. 6A to exemplary hollow legs 142 are in position against the interior wall of the renal artery. Two exemplary hypo-tubes 175 are shown exiting out of the opening 152 and the hollow leg 142 and penetrating through the renal artery wall. In this illustrated embodiment, the element of the hypotubes are the plurality of injection ports 192. Shown in use, the injection port 192 are used to deliver, spray or inject a therapeutic fluid 94. As shown in this illustrative embodiment the fluid 94 is injected into a position outside of the renal artery wall and on an inferior aspect of renal nerves 16. As described herein, the shape, size, length, and curvature of one or more hypotubes 175 may be varied and tailored in order to use the predetermined injection location along with hypotube characteristics to place the element or elements of the hypotube into any of a wide variety of positions relative to a therapeutic target.

It is to be appreciated that the relative positions of the delivery catheter distal end 84, the distal most end 146 of the hollow legs 142, the relative position thereto of the opening 152 along with the characteristics of a hypotube 175 may all be used to determine the delivery sequence, placement and positioning of these components along with the selections of a predetermined injection location in order to provide precise placement of one or more hypotube borne elements 190. In FIG. 6A, the predetermined injection location is opposite the opening 152. Knowledge of the relationship and geometries between these components provides a user with the ability to place the catheter distal end 84, the hollow leg distal end 148 or marker 150 so as to position the hollow leg opening 152 into a position that—after factoring in the hypotube geometry, trajectory and type of element(s)—a hypotube exiting a hollow leg opening in its final position leg opening to penetrate at the predetermined injection location will place the one or more elements it is carrying in a therapeutic range to a therapeutic target. The target area and therapeutic range will vary according to application and the number type and position of element or elements 190 used on a hypotube 175. An exemplary renal artery placement to treat sympathetic nerves adjacent the renal arteries is illustrated in FIG. 6A. In still other applications, a hypotube could exit the sidewall, or distal end as desired for deployment trajectory into hollow organs, veins, arteries, glands, ducts or portions of the alimentary canal, within a lumen of a vessel of an organ or part of an organ. In still further alternatives, the hypotube could exit out of the distal most end of the hollow leg. While shown as used in soft tissue, the characteristics of a hypotube including the tip and rigidity of the body could be adjusted to provide hypotube designs and construction, and material selection and ejection force adjustments to allow introduction of one or more hypotubes and elements 194 positioning into the vasculature, ligaments, muscles, interstitial spaces, or bone, for example.

Figure 6B:
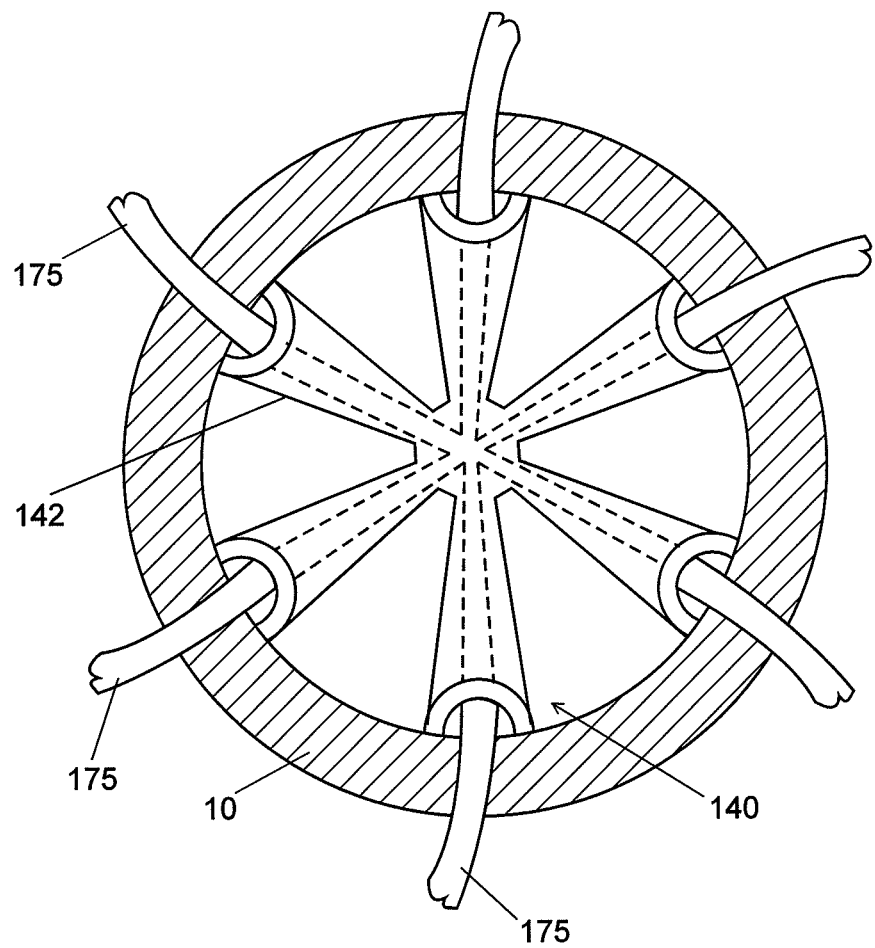
FIG. 6B is an end view of the therapy device of FIG. 6A showing the hypotubes advancing out of the opening in the hollow legs of the positioning device and through the lumen wall.

FIG. 6B is an end view of the therapy device of FIG. 6A showing the hypotubes advancing out of the opening in the hollow legs of the positioning device and through the lumen wall.

In an additional alternative embodiment of FIG. 6B, different elements 190 may be provided on each hypotube 175 and the selection of elements may vary depending upon the hollow leg within which the hypotube is deployed. The embodiment of FIG. 6B shows 6 hollow legs 142 in the positioning device 140. More or fewer legs 142 may be provided such as two, three, four, five, seven, eight, nine, ten or more depending upon the size of the therapeutic site and the number and size of hypotubes to be delivered and the action or therapy to be performed.

Returning to FIG. 6B, the legs are shown (with reference to a clock face) at the 12 o'clock, 2 o'clock, 4 o'clock, 6 o'clock, 8 o'clock and 10 o'clock positions. As described herein, a wide variety of elements 190 may be provided on any hypotube or there may be no lumen in the hypotube such that it acts like an anchor. A hollow hypotube may also be used as an anchor when the lumen is not used or even when the lumen is used to inject or deliver fluid. Hypotube elements may also be selected based on position of or elements on other hypotubes or on the location of a particular hypotube or hypotubes to a therapeutic target. In one embodiment, the hypotubes simply alternate between those with elements 190 for therapy and those without elements (i.e., either solid hypotube or lumens not used to inject). In one embodiment, anchors are at 12, 4 and 8 o'clock positions with active treatment elements at 2, 6 and 10 o'clock. In another alternative, there are anchors at 2, 4, 8 and 10 o'clock with active elements at 12 and 6 o'clock. In still another embodiment, all of the hypotubes have elements but the mode is mixed such as some with electrodes and others with injection ports or combinations thereof. In still another alternative, there is provided some hypotubes for ablation and other for sensing the result of the ablation. For example, one hypotube location or two or more may be for conducting the ablation while one or two or more other hypotubes are provided with sensors for measuring electrical activity or sensing a signal of the body indicating the reduction, loss or interpretations of a neural signal. The output of such measurements may be provided at a handle or display as part of the overall system (see FIG. 5).

Figure 6C:
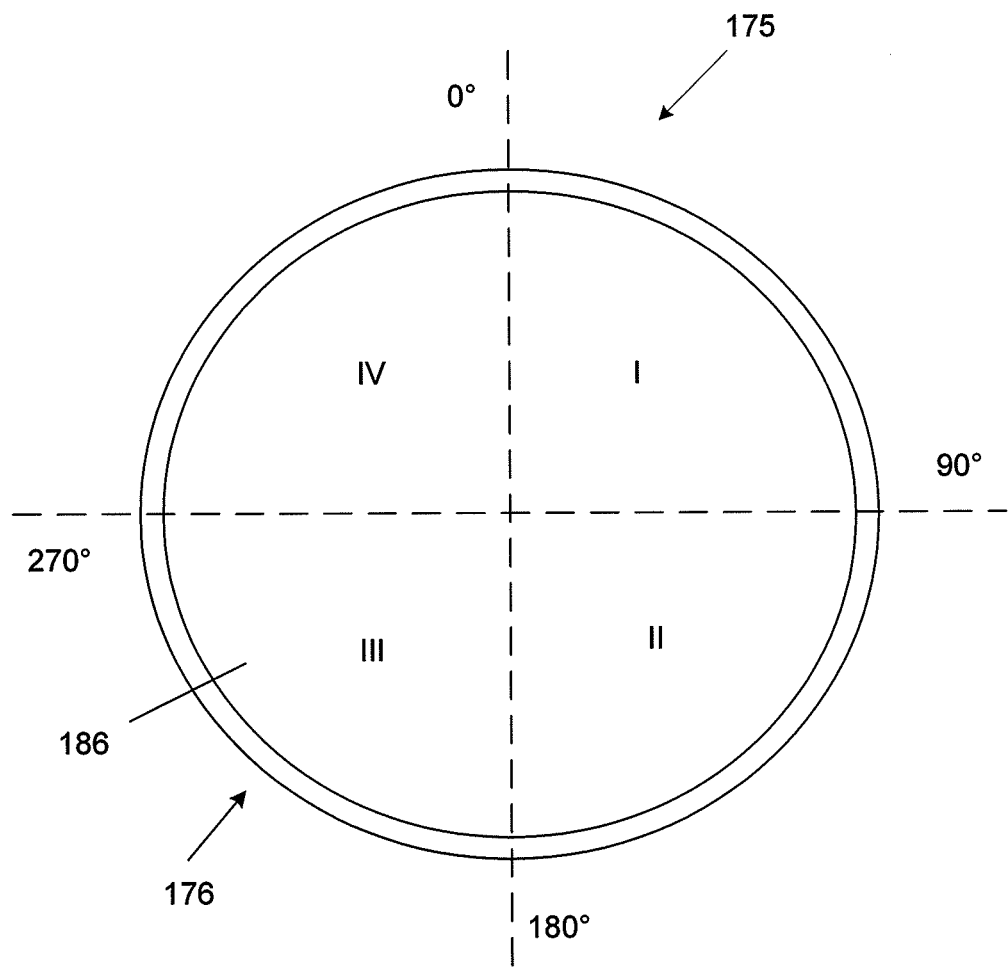
FIG. 6C is an end view of a hypotube showing a coordinate system for describing the location of elements.

FIG. 6C is an end on proximal facing view of a cross-section through the body 176 of a representative hypotube 175. The perimeter of the body 176 is divided into 4 quadrants (I, II, II and IV) in equally divided 90° segments. Embodiments of the elements described herein may be arranged on, in or within a hypotube body 176. An element of a first type may be placed in one quadrant in the same or a different type of element may be placed in an adjacent quadrant or an opposite quadrant. By way of example, of placing the same type of elements, consider an injection port or ports that are formed in a hypotube sidewall of quadrant I. Another set of port or ports may be formed in the adjacent quadrants IV or II or in the opposite quadrant III. Another example would include a mixed mode hypotube where two or more different types of elements are positioned in one or more of the quadrants. Consider for example the positioning of an ablation element in quadrant I and then the positioning of a sensing element (a temperature sensor, impedance monitor, and/or sensing electrode, for example) in the adjacent quadrants II and IV or in the opposite quadrant III. As described above, elements may also be placed at the boundaries between 2 quadrants, in other words at the 0°, 90°, 180°, or 270° positions. In still further alternative embodiments, the positioning of one or more elements or types of elements along the outer radius of a hypotube may be considered positioning the element or elements along the 0° position as indicated in FIG. 6C. In still further alternatives, the placement of an element or elements along the inner radius of a hypotube may be considered the placement of those element or elements along the 180° position illustrated in FIG. 6C.

Figure 13A:
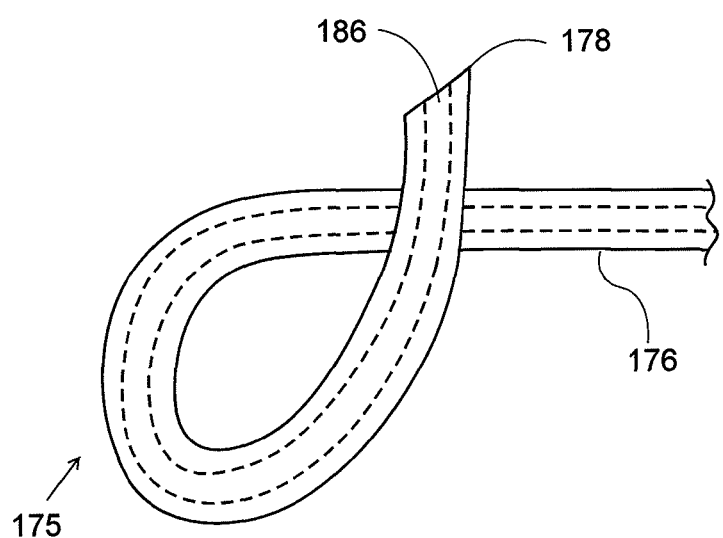
FIG. 13A is a side view of a shaped hypotube extended with a curvature to form a closed loop and also shows a lumen that remains open after curving into a loop.
Figure 13B:
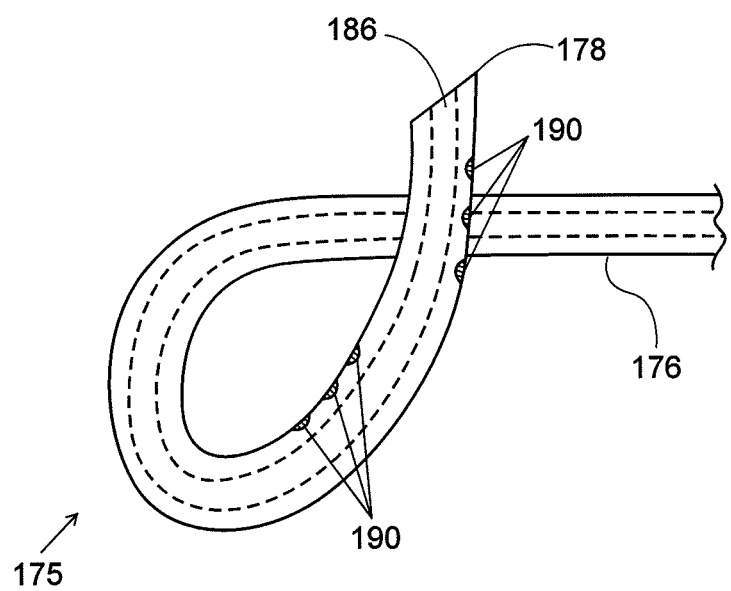
FIG. 13B is a side view of a shaped hypotube extended with a curvature to form a closed loop with an open lumen as in FIG. 13A showing also a group of elements on the hypotube outer radius and a group of elements on the hypotube inner radius.

In the embodiment of FIG. 13B, those elements 190 nearest the distal end along the outer radious would be along the 0° position in FIG. 6C while those elements 190 on the inner radius would be along the 180° position in FIG. 6C.

The apparatus 300 illustrated in FIG. 5 includes external electrode activation circuitry 320 which comprises power control circuitry 322 and timing control circuitry 324. The external electrode activation circuitry 320, which includes an RF generator, is coupled to temperature measuring circuitry 328 and may be coupled to an optional impedance sensor 326. The delivery system 100 and/or catheter 80 incorporates a lumen arrangement configured for receiving a variety of elements or components, such as conductors, electrodes, pharmacological agents, heating elements, transducers, sensors, or other components as needed or described herein for the various therapeutic applications and treatment sites.

The RF generator of the external electrode activation circuitry 320 may include an external pad electrode 330 configured to comfortably engage the patient's back or other portion of the body near the kidneys when used for renal denervation. Radiofrequency energy produced by the RF generator is coupled to the element 190 at the distal end 178 of the hypotube 175 by a conductor arrangement 191 disposed in the lumen 186.

Renal denervation therapy using the apparatus shown in FIG. 5 is typically performed using the electrode assemblies 194 of the hypotube 175 positioned within the renal artery 12 and the external pad electrode 330 positioned on the patient's back, with the RF generator operating in a unipolar mode. In this implementation, the electrode assemblies 194 are configured for operation in a unipolar configuration. In other implementations, the electrode assemblies 194 can be configured for operation in a bipolar configuration, in which case the external electrode pad 330 is not needed. The radiofrequency energy flows through the electrode assemblies in accordance with a predetermined activation sequence (e.g., sequential or concurrent) selected based upon the position of the electrodes 194 or elements to the therapeutic target (See FIGS. 14A-C, 13, 15, 16, 17 and 18). Application of RF energy alone or in combination with the operation of other elements to deliver a drug or monitor the progress or effectiveness of the therapy (i.e., the diminution, increase or cessation of neural activity or activation levels before, during or after application of ablation, stimulation or modulation energy via one or more elements) then ablates, stimulates, or modulates target tissue, which includes renal nerves.

According to some embodiments, the electrode activation circuitry 320 is configured to control activation and deactivation of the electrode assemblies 194 in accordance with a predetermined energy delivery protocol and in response to signals received from temperature measuring circuitry 328. The electrode activation circuitry 320 controls radiofrequency energy delivered to the electrode assemblies 194 so as to maintain the current densities at a level sufficient to cause heating of the target tissue to at least a temperature of 55° C.

In one embodiment, element 190 is one or more temperature sensors situated at or in the hypotube lumen 186 to provide for continuous or intermittent monitoring of renal artery tissue temperatures, and RF generator power is automatically adjusted so that the target temperatures are achieved and maintained. In addition or alternatively, an element 190 may be an impedance sensor arrangement used to measure and monitor electrical impedance during RF denervation therapy, and the power and timing of the RF generator 320 may be moderated based on the impedance measurements or a combination of impedance and temperature measurements provided by hypotube borne elements. The size of the ablated area is determined largely by the size, number, and shape of the hypotube borne elements (such as electrodes or electrode sets) the power applied, and the duration of time the energy is applied.

Embodiments of the disclosure are directed to apparatuses and methods for performing an action on, to or with a target tissue of the body, such as innervated tissue, cardiac tissue, organ tissue, vessels, tumors, and diseased tissue (internal and external). In one aspect, there are embodiments of the disclosure are directed to apparatuses and methods for ablating perivascular renal nerves for the treatment of hypertension. In still other aspects, there are provided apparatuses and methods are directed to a shaped or deformable hypotube based ablation system and use of same for delivering ablation therapy to target tissue within the body.

Various embodiments of the disclosure can contain radiopaque markers 150 placed at the distal ends 148 of the hollow legs 142 to provide visibility for positioning the hollow legs 142 in an area proximal to the target tissue and for aiding in aligning opening with predetermined location as described herein.

The delivery system can be fabricated to include support structures such as a braid, a ribbon coil, etc., to provide the mechanical characteristics necessary to get the delivery system to the desired treatment location. In various alternative embodiments, a helical coiled ribbon could be used to provide axial stiffness with flexibility in order to navigate to areas proximal to the target tissue, In one embodiment, flexible element 356 is such a feature which allows the delivery system to navigate the bend from the aorta to the renal artery. In various alternative embodiments, the delivery catheter includes a homeostasis valve 124 with a sideport 120 for flushing of the catheter and a coaxial dilator for delivering the sheath to the appropriate location for deployment of the therapeutic device (see FIG. 7).

Various embodiments of the disclosure are directed to ablation apparatuses and methods of ablation which include or use a shaped or deformable hypotube based ablation system preferably configured for hand-held manipulation. Various embodiments are directed to ablation apparatuses and methods of ablation which include or use a shaped or deformable hypotube based ablation system in combination with an external patient monitor. According to some embodiments, a hypotube based ablation catheter includes an RF ablation arrangement in combination with a fluid delivery port, ports or injection site. In other embodiments, an element of a hypotube based therapy system includes an ultrasound element alone or in combination with other elements described herein.

In one or more various embodiments which incorporate an RF ablation arrangement, an efficient switching power supply is configured to operate as a representative RF generator. Similar circuitry can be implemented for hypotube based renal nerve ablation devices that employ a microwave generator according to other embodiments as well as for other modalities such as ultrasound or sensing arrangements or monitors.

In various alternative embodiments, a cooling apparatus or mechanism or injection of cooling gas or fluid via a lumen of the system is used to cool the ablation region or region of therapy to spare tissues adjacent the hypotube element from excessive heat and/or project heat deeper into the arterial wall or other therapeutic site or in proximity of the renal nerves or other target. It is noted that various element embodiments which incorporate an ultrasound ablation arrangement may not need a cooling mechanism due to the enhanced ability to focus ultrasound energy at target tissue without a thermally damaging intervening tissue. Cooling may be provided within, through or via one or more lumens of the system or by a circulating gas or fluid and/or by a gas phase change or Joule-Thompson effect cooling at the tip, for example. Elements used in conjunction with hypotubes may be one or more of thermocouples, unipolar or bipolar electrode arrangements or other sensors can be incorporated into one or more element regions located on, along, within, or via one or more hypotubes in any combination. In addition, the delivery catheter 80 and delivery system 100 including the positioning device 140 (including hypotubes 175) may be delivered within the body to any location to position one or more hypotube elements for therapy using over-the-wire, fixed-wire, or no-wire systems can be used, with guiding sheaths or catheters as needed.

In one aspect, hypotube based elements, devices and configurations are provided to replace other conventional RF ablation applications such as ablation of cardiac tissue for arrhythmia treatment, renal denervation using high frequency AC energy (e.g., RF or microwave energy) and other such ablative therapies within the body. The number of lesions required in a procedure typically varies and can range from 2, 4, 6, 8, 10 or more depending upon the size and arrangement of the treatment site. The lesions may be formed in symmetric or asymmetric patterns about a lumen, organ or other site depending upon the desired therapeutic outcome. In one specific embodiment, the number of lesion sites treated by the hypotube delivery system does not exceed eight, four in each renal artery.

In one exemplary technique, the delivery catheter 80 is positioned in the vessel selected to place the hypotube elements in the desired location for the therapy or action. Next, the positioning device 140 is advanced out of the delivery catheter to place each of the legs 142 into apposition with the inner lumen wall. Next, the hypotubes 175 are advanced from within each of the legs out of the lumen 154, through the lumen wall and into a final position. The final position is that position where the one or more elements 190 on the hypotubes are positioned for the desired therapy. Next, the therapy or action is performed using the elements 190. Thereafter, the hypotubes are within drawn into the hollow leg lumen 154, the positioning device 140 is manipulated to place the openings 152 into position to deploy the hypotube elements 190 into the next therapy or action position by advancing, withdrawing or rotating the positioning device 140. Once in the next position, the hypotubes are again advanced until the elements 190 are in position to deliver the desired therapy. This process of advancing and withdrawing the hypotubes and adjusting the position of the positioning device is repeated as needed until the therapy or action is completed.

As described herein, the hypotube tip 178 or body 176 may shaped, sized or selected based on a number of factors such as the used of the hypotube 175 to have the tip 178 or a portion of body 176 to be positioned on, in or within one or more tissue sites during the use of one or more elements. It is to be appreciated that the tip, body, length, curvature and other design characteristics of the hypotube may be selected in order to stabilize the delivery system 100 during use. This particular variable anchoring aspect of the device is particularly useful when treating structures of the body that move during treatment. Examples include, organs, portions of the alimentary canal as well as portions of the vasculature as well as tissue and structures within the retroperitoneal space or peritoneal cavity that move with the movement of the diaphragm. In one particular aspect, the hypotubes are sized and shaped to anchor the delivery system 100 during used in the renal artery to stabilize in response to renal artery movement and bending motion during respiration. The positional change of the arteries during respiration induced both bending and change in angulation of the renal arteries. This bending can have a complex three dimensional shape near the ostia as further described in "Three Dimensional Analysis of Renal Artery Bending Motion During Respiration" by Mary T. Draney, et al (J. Endovasc. Ther., 2005; 12:380-386), incorporated herein by reference for all purposes.

Figure 7:
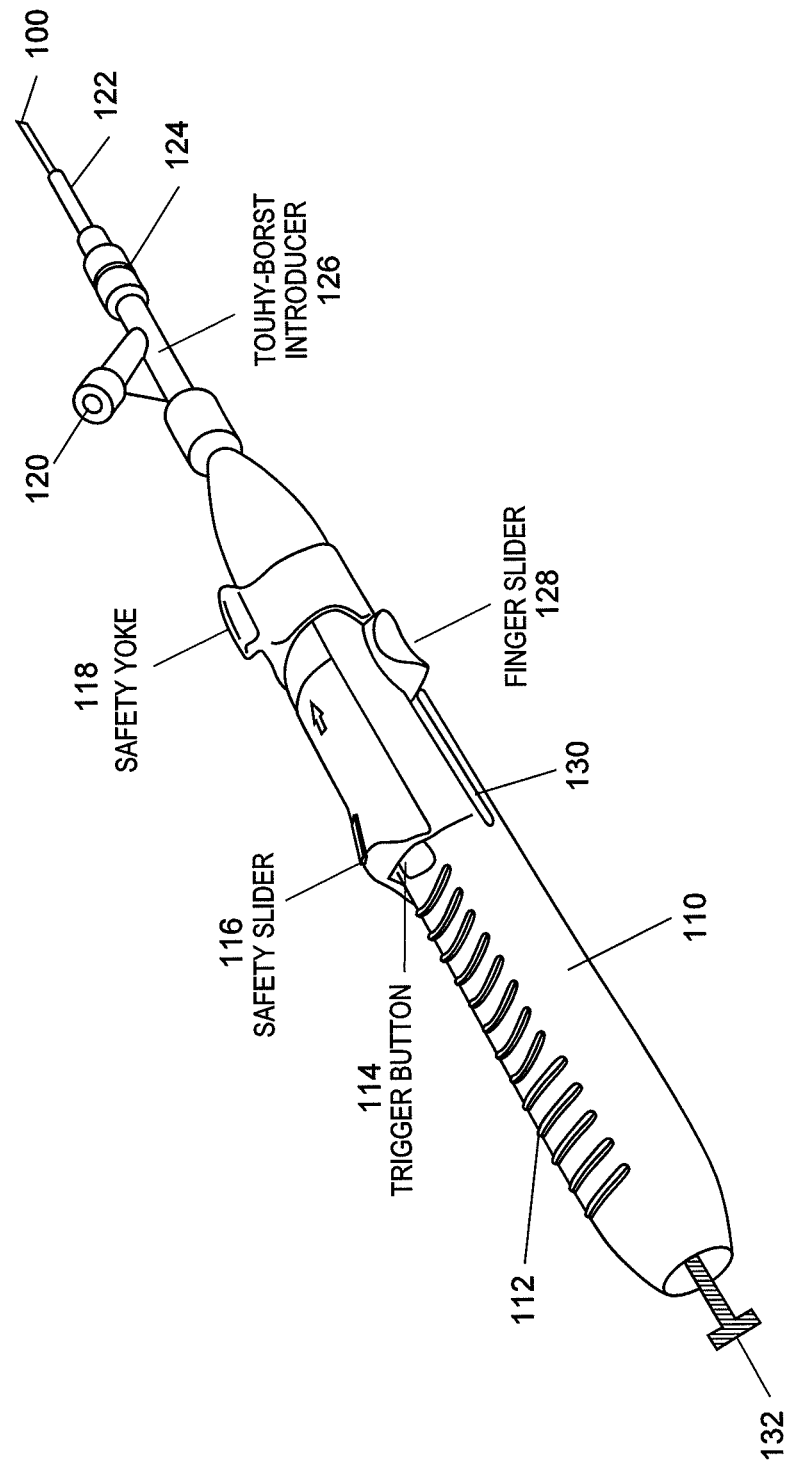
FIG. 7 is an isometric view of an embodiment of a handle used in conjunction with the operation of the delivery system described herein.

FIG. 7 is an isometric view of an embodiment of a handle 110 used in conjunction with the operation of the delivery system described herein. The handle 110 includes a grip 112, trigger button 114, a safety slider 116, a safety yoke 118 and a finger slider 128 within a slot or groove 130. The handle is connected to a Touhy-Borst introducer 126 having a flush port 120 and also a rotating hemostasis valve 124. Distal to the valve 124 is a sheath 122 over the delivery device 100. The delivery catheter 80 is not shown but would be positioned over the delivery device 100. The handle 110 provides connections as needed for connecting each of the hypotube element/fluid delivery structures with a fluid, gas, or electrical passageway depending on the element type in each hypotube 175. The handle 110 also includes a port 132 for injecting a fluid, or gas, or passing an electrical connection through the lumen or lumens in communication with the hypotube lumen 186.

The finger slider is pulled proximally along the slot to cock a spring based firing mechanism in one embodiment. This pulls the hypotube into their respective hollow legs. At this point, the trigger button is armed but covered by the safety slider. Once the delivery system is in place (i.e., the opening of the hollow leg is in the predetermined location for delivery of the hypotubes) the safety yoke is moved to permit motion of the safety slider to expose the trigger button. When ready to deliver the hypotubes, the trigger button is pressed and the hypotubes are ejected from the hollow legs using the force of the delivery system.

In still other aspects, the hypotube structure or device or element has a lumen in communication with the handle lumen or port 132 through which biologic, therapeutic, or other fluid, or gas, agents can be administered via one or more hypotubes. In still other aspects, the hypotube structure or device or element has the ability to detect and/or administer electrical signals. In still other aspects, the hypotube structure or device or element is comprised of solid cylindrical, tubular, or barbed structure.

In addition to the features shown in FIG. 5, the delivery system includes an appropriate drive system coupled to one or both of the drive tube 144 and the drive hub 177 that can be actuated using a handle, trigger, latch release or suitably equipped handle in any of the following ways:

i. Mechanically e.g., simple push-pull action, spring driven, or screw driven, and the like; or,
  ii. Electromechanically e.g., solenoid driven, piezoelectric actuated, voice coil, motor driven, and the like; or,
  iii. Hydraulically e.g., fluid or gas driven or via a piston driver.

Figure 8:
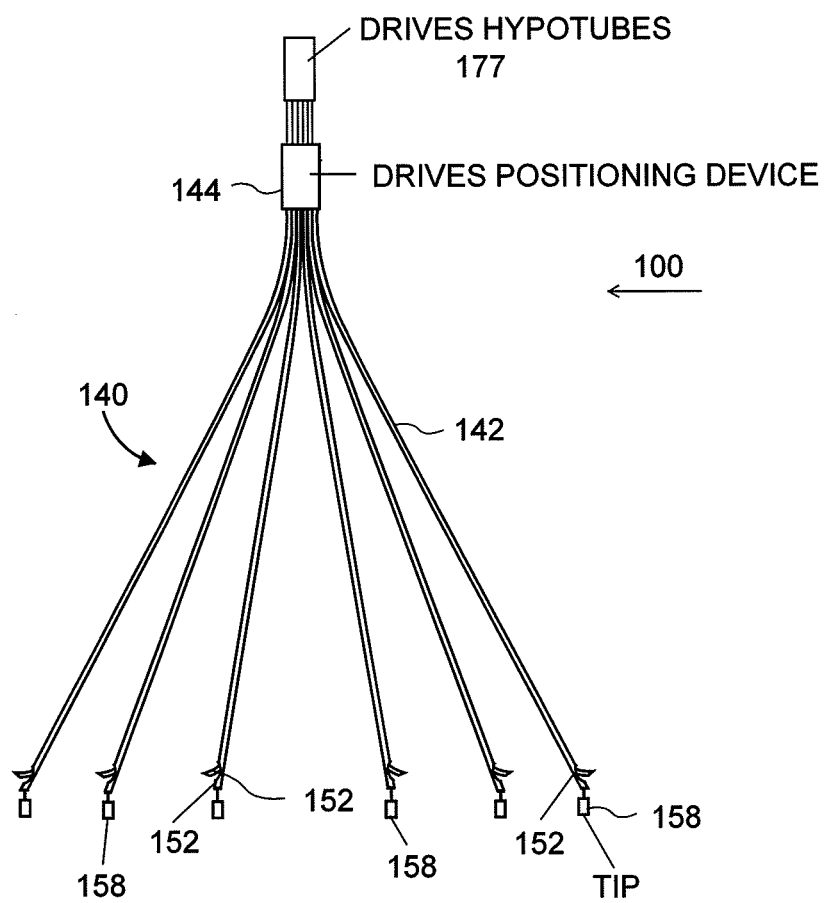
FIG. 8 is a side view of the delivery device showing the hollow legs connected to a first hub and the hypotubes connect to a second hub.

FIG. 8 is a side view of the delivery device 100 showing the hollow legs 142 connected to a first hub 144 and in the hypotubes connect to a second hub 177.

Embodiments of the disclosure are comprised of a positioning device 140 with integral centering mechanism (optional-shown in FIG. 19), and hypotubes 175 with delivery elements 190. According to some embodiments the positioning device 140 is a simple tubular catheter designed, depending on the application, to be located at the intended site of treatment and comprising a multi-component system that provides for flushing and delivery of the appropriate therapeutic solution, gas, or current to the elements 190 located at the distal end of the hypotubes 175 which are advanced through the positioning system.

In one aspect, the positioning device 140 is comprised of plurality of hollow legs 142 made of nitinol or other materials that emanate from a central proximal position located near the distal end 84 of a delivery catheter 80. Each leg 142 may have a distal end opening 146 or a side opening 152 to accommodate the hypotubes 175, depending on the application. For renal artery nerve ablation, a sidewall opening 152 is preferable. The proximal portion of the positioning system are brought together at a sleeve 144 composed of polymer or metal that holds the hollow legs 142 in the proper radial orientation without obstructing their lumens 154. In various embodiments, each hollow leg 142 may be formed so that the distal end 146 bends slightly inwards at the level of the side opening 152 with a small extension beyond the opening 152 that keeps the positioning system from penetrating the wall of the renal artery or other lumen.

FIG. 9A is an enlarged side view of a distal portion of a hollow leg of FIG. 6A showing a hypotube tip just exiting an opening in the hollow leg sidewall.

FIG. 9B is a top view of the distal portion of a hollow leg and end cap without a hypotube inside the lumen of the hollow leg through an opening in the hollow leg sidewall FIG. 9C is a top view of an alternative distal hollow leg portion of a hollow leg without a hypotube inside the lumen of the hollow leg through an opening in a sidewall of the hollow leg and a filled lumen at the furthest distal portion of the hollow leg.

Figure 9D:
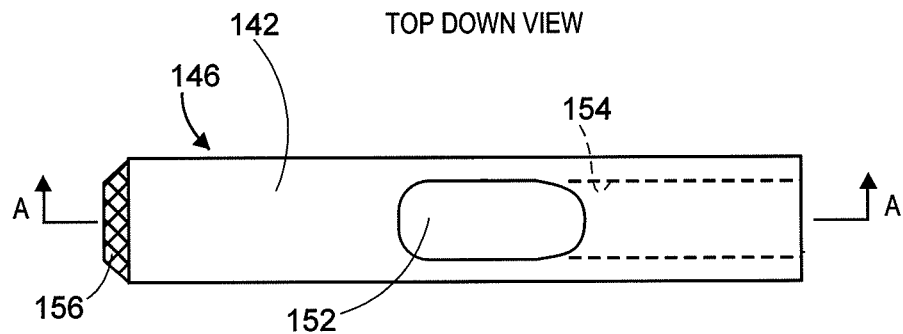
FIG. 9D is an alternative view of FIG. 9C showing the location of a hollow leg lumen relative to the sidewall opening and an alternative flattened end.

FIG. 9D is an alternative view of FIG. 9C showing the location of a hollow leg lumen relative to the sidewall opening and an alternative flattened end.

Figure 9E:
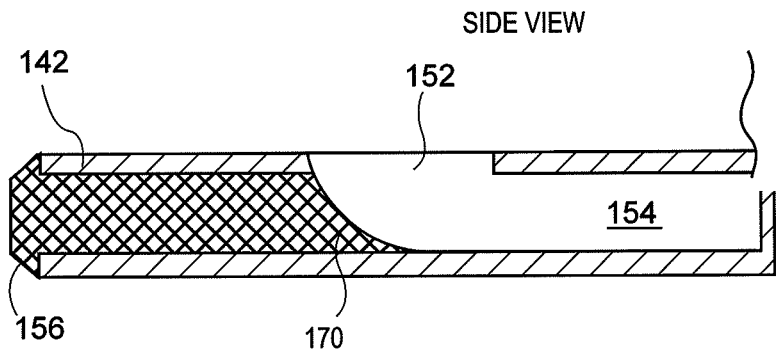
FIG. 9E is a side view of FIG. 9D showing fill material or, alternative insert plug to close off the end of the hollow leg lumen and align the shaped surface with sidewall opening.

FIG. 9E is a side view of FIG. 9D showing fill material or, alternative insert plug to close off the end of the hollow leg lumen and align the shaped surface 170 with sidewall opening 152.

Figure 9F:
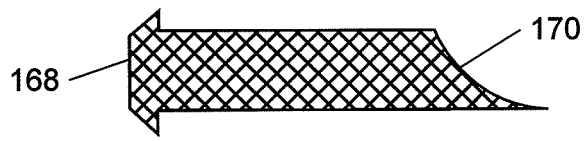
FIG. 9F is the fill material or insert plug of FIG. 9E.

FIG. 9F is the fill material 168 or insert plug of FIG. 9E.

Figure 9G:
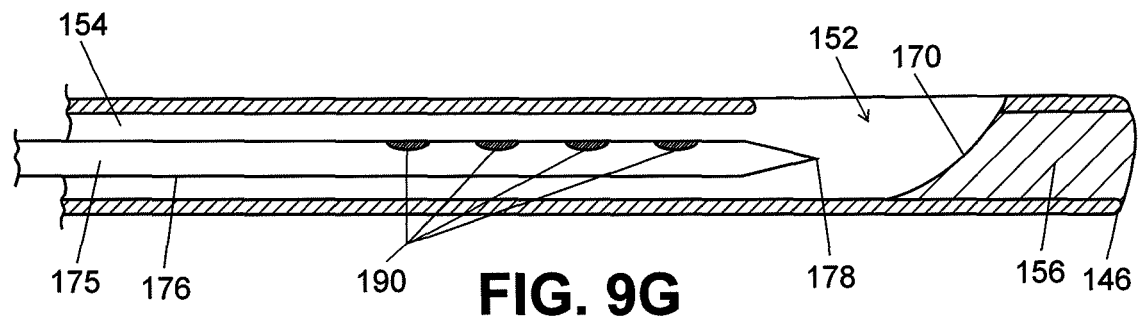
FIG. 9G is a side view of FIG. 9C showing fill material or a plug with an alternative shaped surface aligned with the sidewall opening and a hypotube within the hollow leg lumen.

FIG. 9G is a side view of FIG. 9C showing fill material or a plug 156 with an alternative shaped surface 170 aligned with the sidewall opening 152 and a hypotube within the hollow leg lumen.

Figure 10:
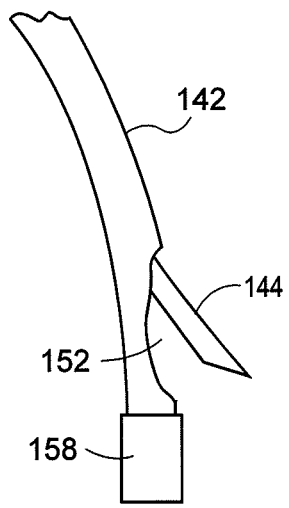
FIG. 10 is a side view of an alternative hollow leg end cap.
Figure 10:
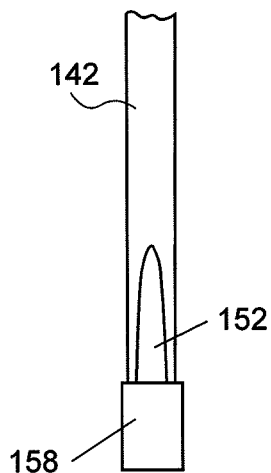
Figure 10:
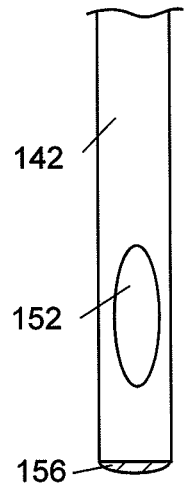
Figure 10:
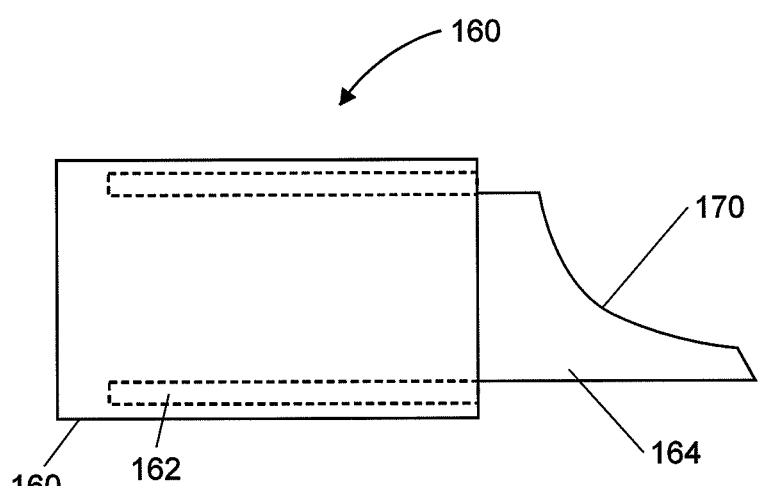

FIG. 10 is a side view of an alternative hollow leg end cap 160. The cap 160 has spacing 162 to accommodate the wall thickness of hollow leg 142. The insert 164 is shaped to fill lumen 154 and align 170 with opening 152.

Figure 11A:
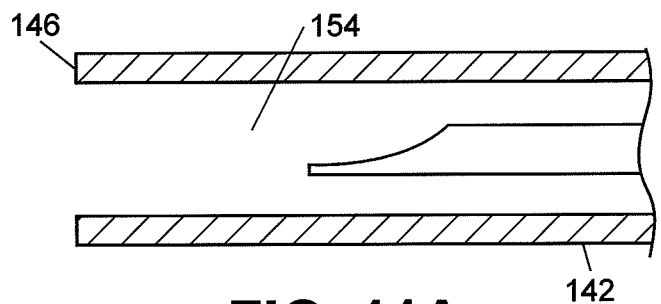
FIG. 11A is a cross section view of an end of a delivery device alternative embodiment where a hypotube is advanced towards and through the opening at the distal most end of a hollow leg as shown in FIG. 11B.
Figure 11B:
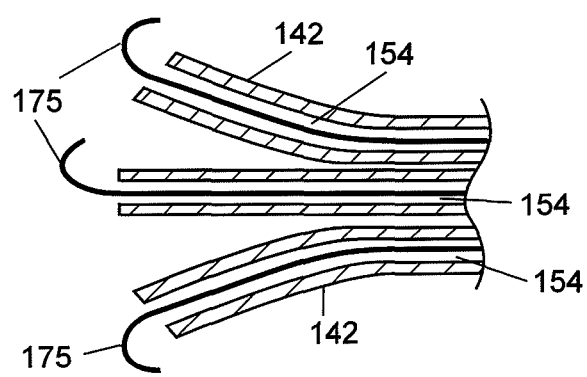
FIG. 11B is a cross section view of a three hollow leg delivery device with three hypotubes delivered from the distal most end of each.

FIG. 11A is a cross section view of an end 146 of a delivery device alternative embodiment where a hypotube 175 is advanced towards and through the opening 154 at the distal most end of a hollow leg 142 as shown in FIG. 11B.

FIG. 11B is a cross section view of a three hollow leg 142 delivery device with three hypotubes 175 delivered from the distal most end 146 of each.

Figure 12A:
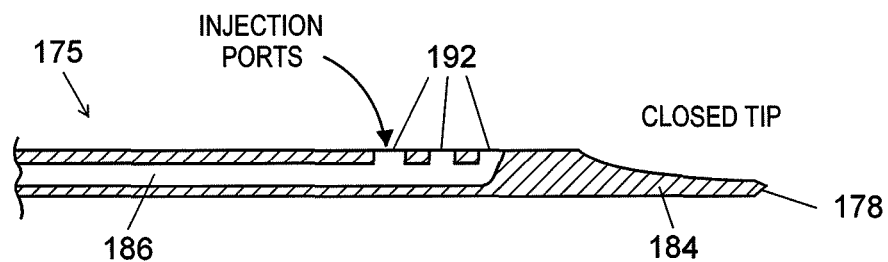
FIG. 12A is a cross section view of the distal end of a hypotube with a closed off distal tip and three injection ports as an element for performing an action.

FIG. 12A is a cross section view of the distal end of a hypotube with a closed off distal tip and three injection ports as an element for performing an action.

Figure 12B:
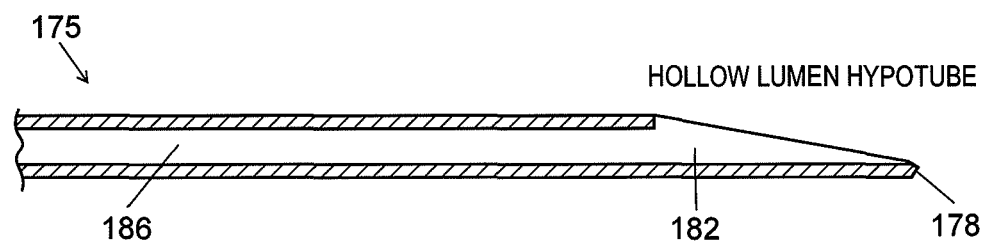
FIG. 12B is a cross section view of a hypotube having a lumen extending to the distal most end.

FIG. 12B is a cross section view of a hypotube having a lumen extending to the distal most end.

Figure 12C:
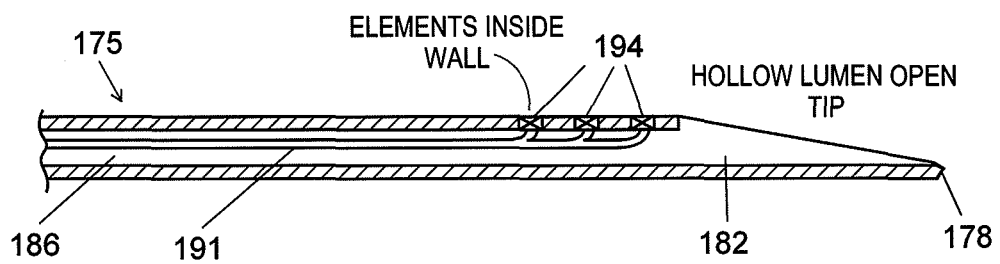
FIG. 12C is a cross section view similar to FIG. 12B that includes three elements within the sidewall of the hypotube and a single connection channel provided to connect the elements to the proximal end of the hypotube.

FIG. 12C is a cross section view similar to FIG. 12B that includes three elements within the sidewall of the hypotube and a single connection channel provided to connect the elements to the proximal end of the hypotube.

FIG. 12D is a cross section view similar to the embodiment of FIG. 12C with injection of a therapeutic fluid through the lumen at the distal most end and three sidewall elements each having separate connection lines to the proximal end of the hypotube.

FIG. 12E is a section view of an alternative hypotube embodiment with a closed tip and having three injection port elements in communication with the hypotube lumen and a separate lumen or cavity containing an additional element within the sidewall of the hypotube.

In one aspect the elements 190 provided by a hypotube are micro EEG devices or sensors suited to detection of the appropriate body signals related to the therapy being delivered. The system shown in FIG. 5 would be modified to include the appropriate addition components for EEG, EKG, or EMG as needed depending on the use of the hypotube therapy system. For example, such EEG sensors may be monitored as an ablation drug or fluid is injected using adjacent or opposite positioned elements. As the ablation progresses, it is believed that the appropriate sensor in one or more hypotubes could be used to detect, monitor, record or otherwise indicate the progress, completion or effectiveness of a therapy delivered using one or more hypotube borne elements.

FIG. 13A is a side view of a shaped hypotube extended with a curvature to form a closed loop and also shows a lumen that remains open after curving into a loop.

FIG. 13B is a side view of a shaped hypotube extended with a curvature to form a closed loop with an open lumen as in FIG. 13A showing also a group of elements on the hypotube outer radius and a group of elements on the hypotube inner radius.

Figure 13C:
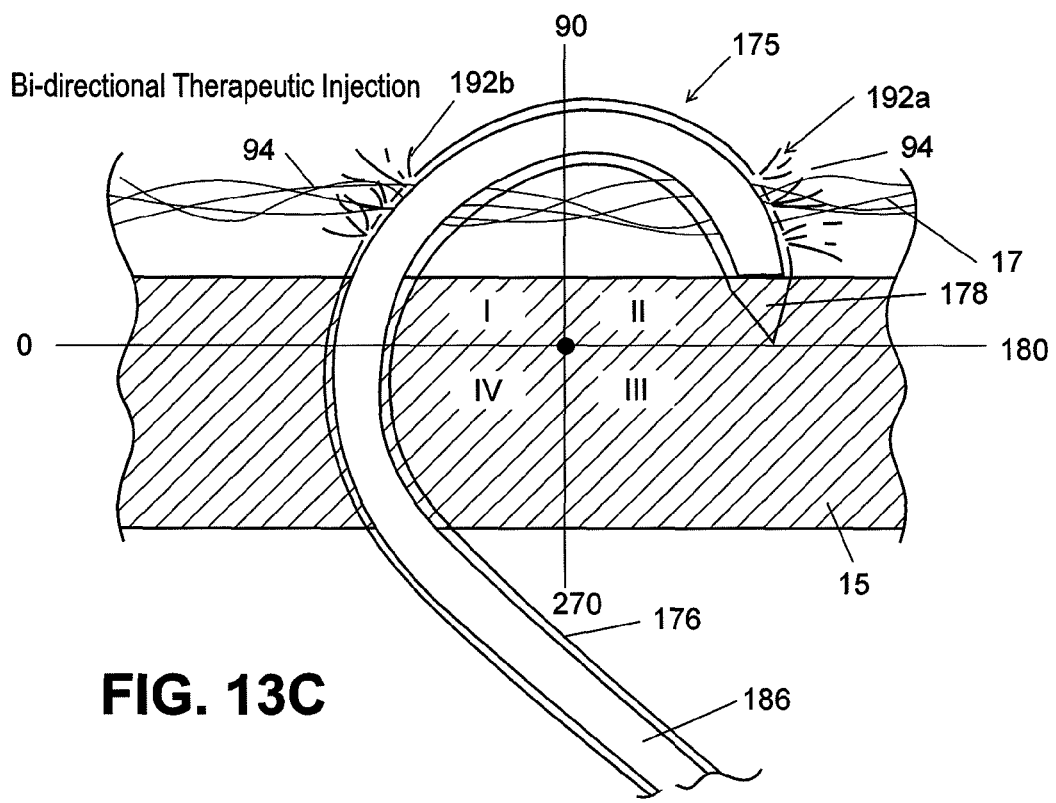
FIG. 13C is a side view of a hypotube in position for delivery of therapy using two sets of spaced apart elements in position for delivery of therapy to multiple positions of a target. Also shown is a coordinate system for describing the location of one or more elements.
Figure 15A:
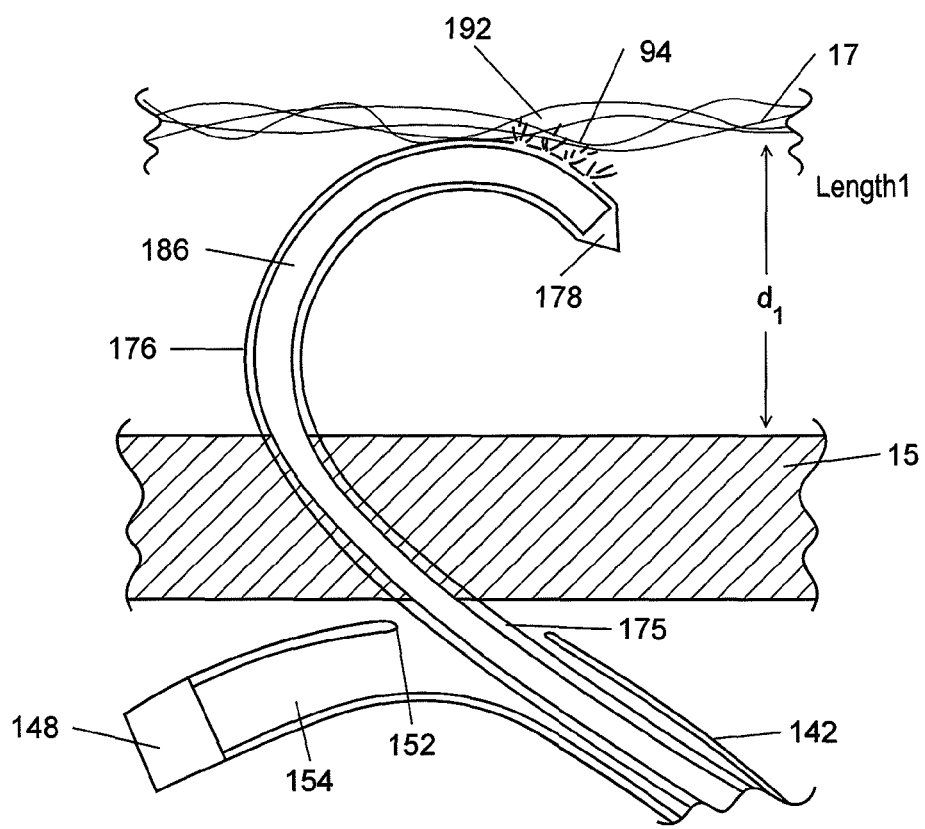
FIG. 15A is a side view of a closed end hypotube in position for delivery of therapy to a target spaced apart from the wall with elements placed generally below the therapeutic target and without penetrating the therapeutic target.

FIGS. 13C, 14A, 14B and 14C also illustrate a coordinate system used for describing the location of one or more elements 190 on, in or within a hypotube 175. The therapeutic hypotube is divided into 4 quadrants with 0°, 180°, and 360° being on the x axis and 90° and 270° on the Y axis. In the example of FIG. 13C, the proximal set of ports 192b will reside between 40°-70° from 0° (in the upper far left quadrant), and the distal ports 192a would reside between 110°-140° (in the upper right hand quadrant). This type of coordinate system is useful since it scales along with to the various hypotube radii, i.e. radius one, two and three. It also works for other applications where the therapeutic hypotubes are extended for different distances, i.e., length one, two, and three as shown in FIGS. 15A, 15B and 15C.

FIG. 13C is a side view of a hypotube in position for delivery of therapy using two sets of spaced apart elements in position for delivery of therapy to multiple positions of a target. As shown in this embodiment, there are ports 192b at about 110°-140° and ports 192a at about 40° to about 70°. Individual ports may be spaced from 3-4 times of the diameter of the hypotube. In another aspect, the spacing is from about 0.021"-0.024".

Figure 13D:
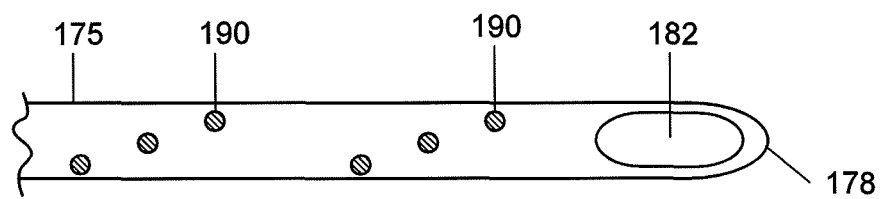
FIG. 13D is a top view of a hypotube showing a repeating spiral pattern of elements along the hypotube longitudinal axis.

FIG. 13D is a top view of a hypotube showing a repeating spiral pattern of elements along the hypotube longitudinal axis.

Figure 13E:
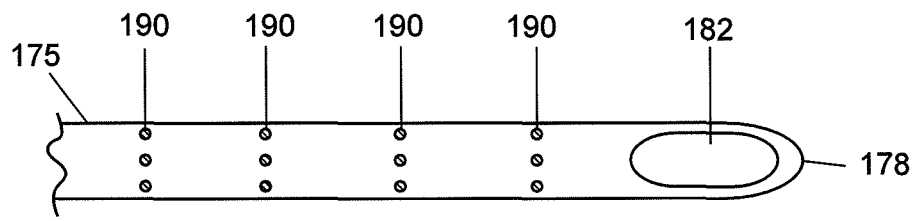
FIG. 13E is a top view of a hypotube showing a repeating pattern of elements generally transverse to the hypotube longitudinal axis.

FIG. 13E is a top view of a hypotube showing a repeating pattern of elements generally transverse to the hypotube longitudinal axis.

Figure 13F:
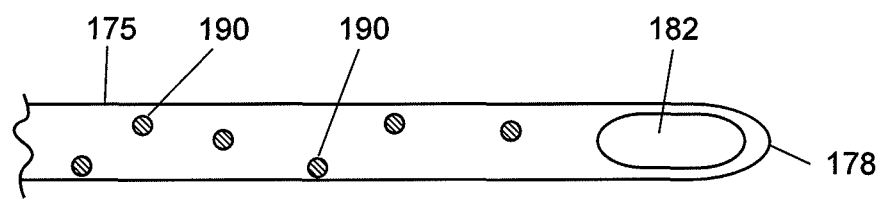
FIG. 13F is a top view of a hypotube showing a pattern of elements along the hypotube longitudinal axis.

FIG. 13F is a top view of a hypotube showing a pattern of elements along the hypotube longitudinal axis.

Figure 14A:
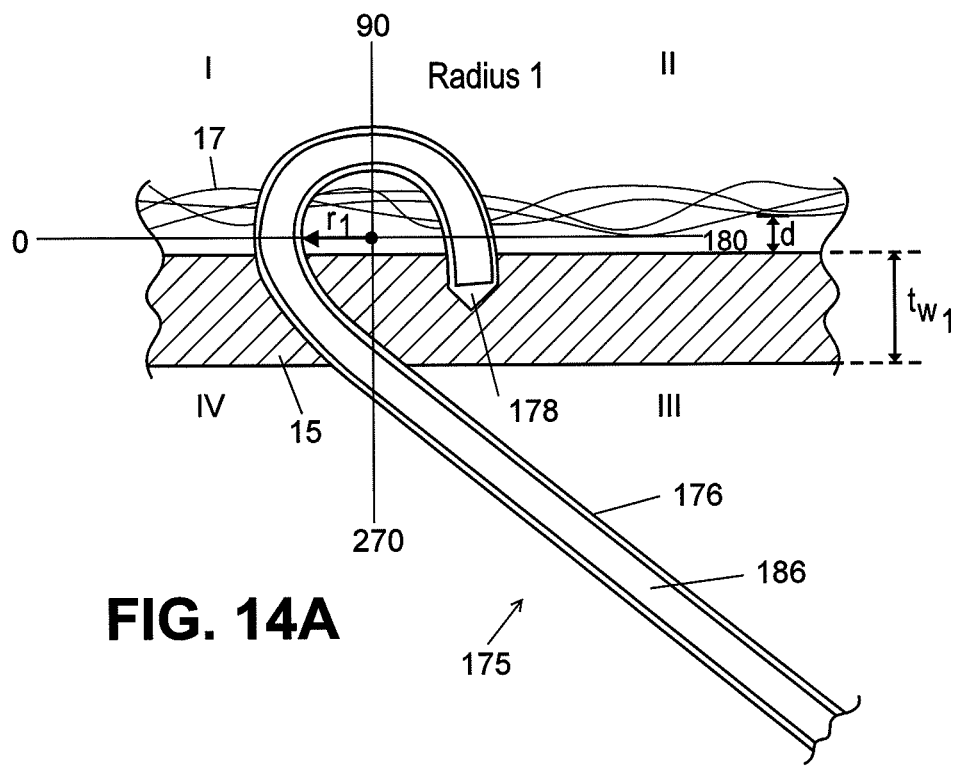
FIG. 14A is a section view of a hypotube forming a first radius of curvature once extended and curved to anchor within a wall of a first thickness.
Figure 15B:
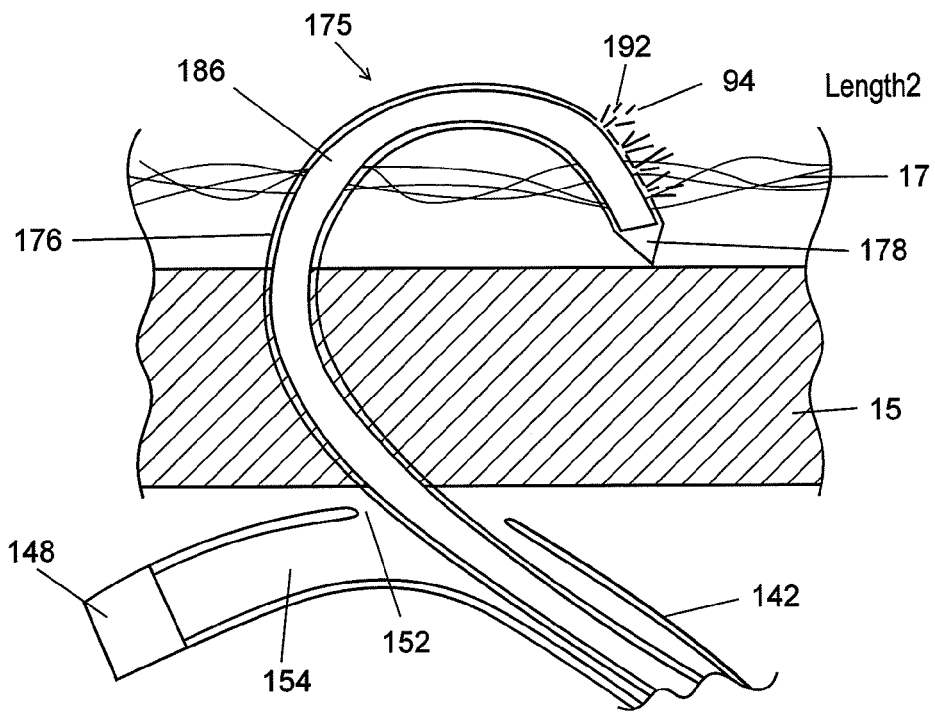
FIG. 15B is a side view of a closed end hypotube in position for delivery of therapy to a target spaced apart from the wall with elements placed generally above or in the therapeutic target without or only slight penetration of the hypotube tip into the outer surface of the wall.
Figure 15C:
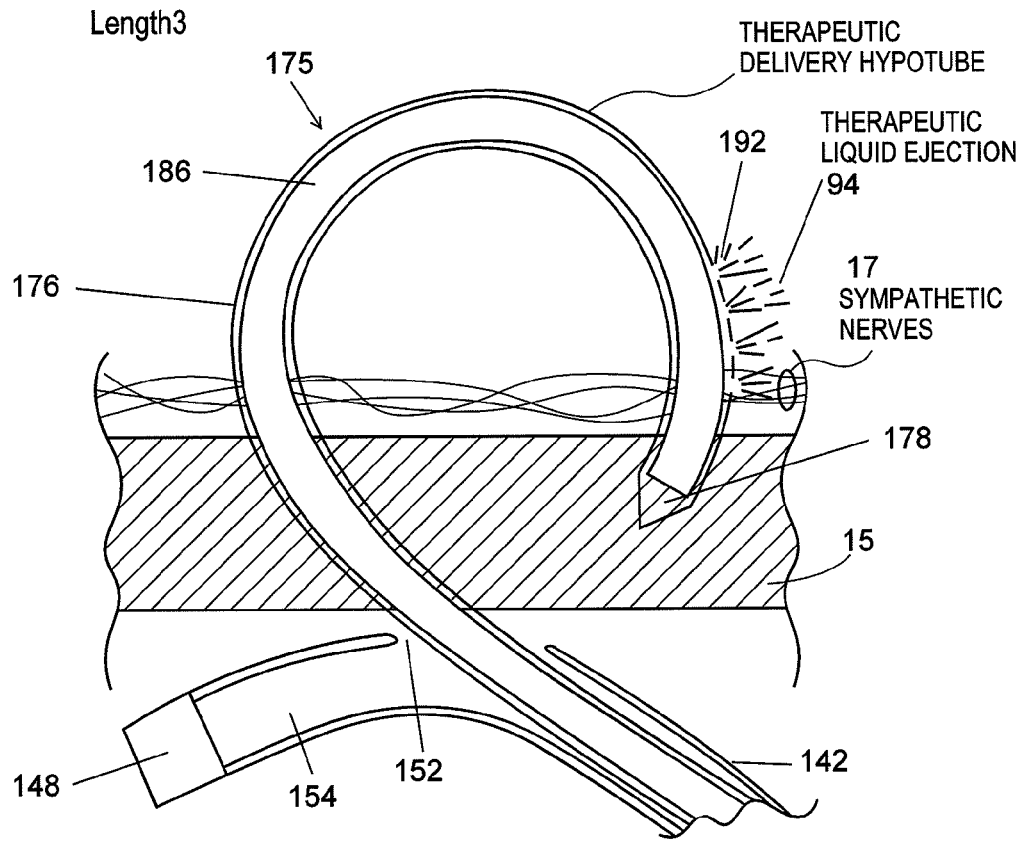
FIG. 15C is a side view of a closed end hypotube in position for delivery of therapy to a target spaced apart from the wall with elements placed generally above or in the therapeutic target with an additional length of the hypotube passed through adjacent tissue and with penetration of the hypotube tip into the outer surface of the wall.

FIG. 14A is a section view of a hypotube forming a first radius of curvature once extended and curved to anchor within a wall of a first thickness.

Figure 14B:
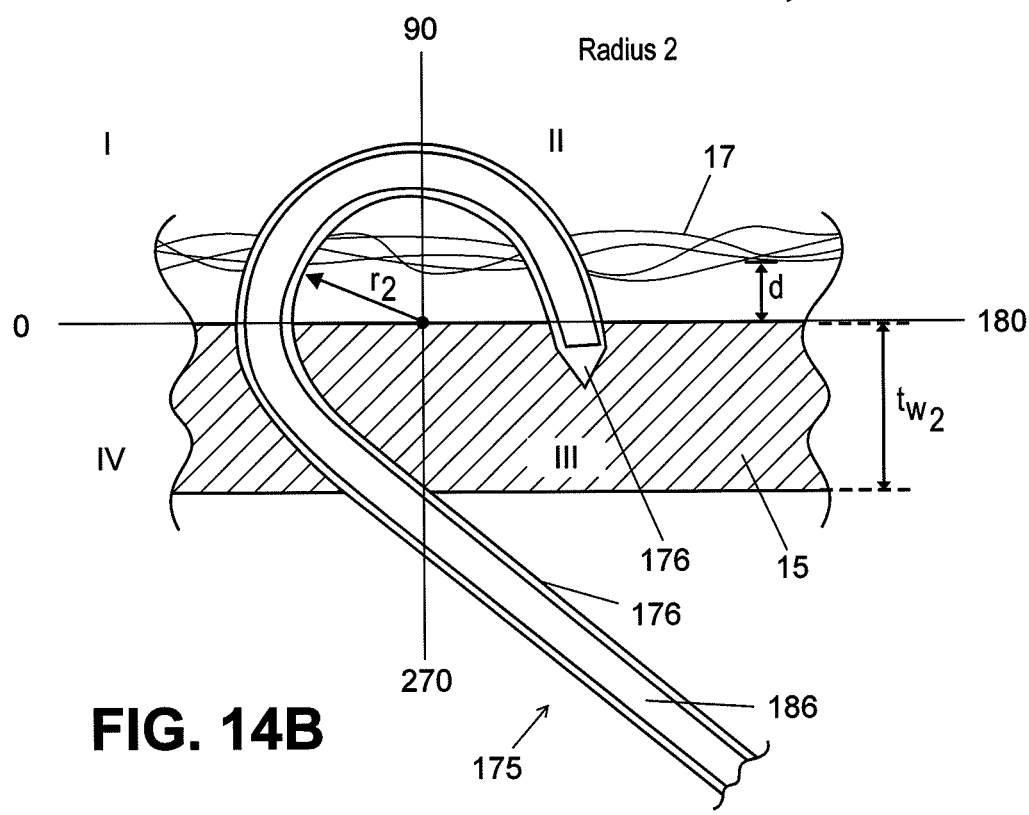
FIG. 14B is a section view of a hypotube forming a second radius of curvature once extended through and curved to anchor within a wall of a second thickness.

FIG. 14B is a section view of a hypotube forming a second radius of curvature once extended and curved to anchor within a wall of a second thickness.

Figure 14C:
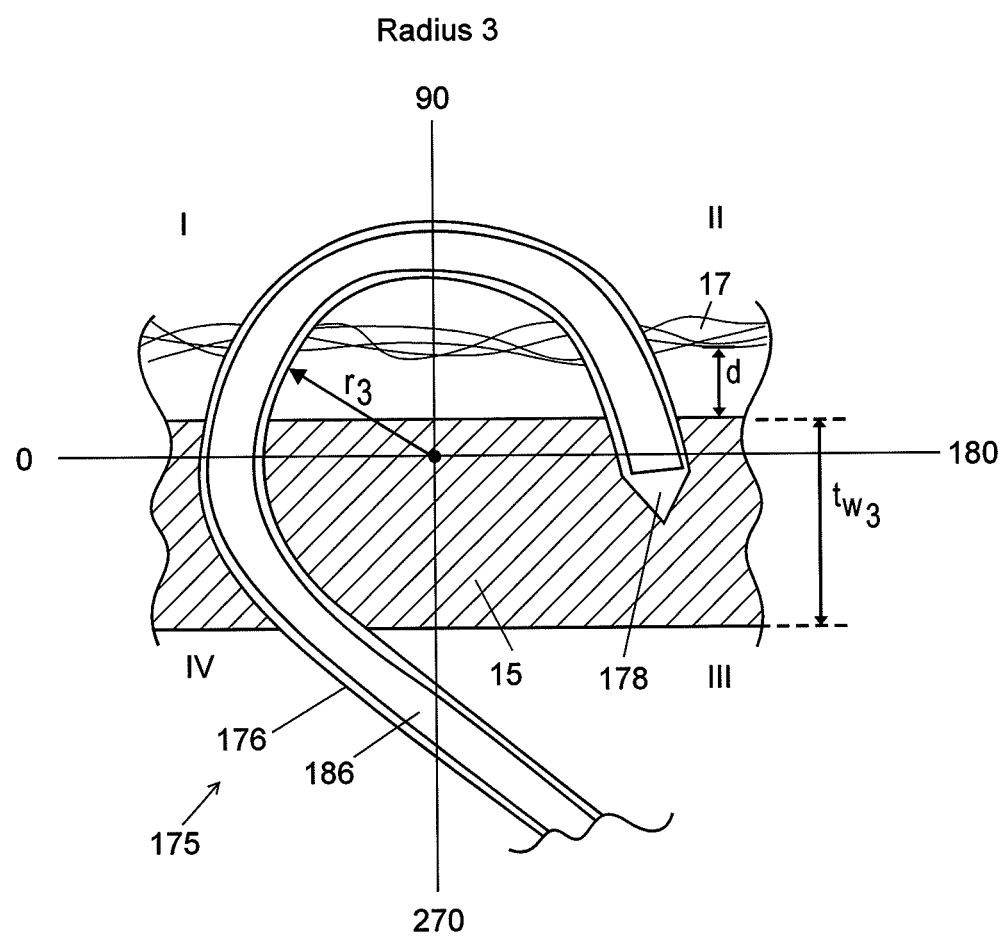
FIG. 14C is a section view of the hypotube forming a third radius of curvature once extended through and curved to anchor within a wall of a third thickness.

FIG. 14C is a section view of the hypotube forming a third radius of curvature once extended and curved anchor within a wall of a third thickness. FIGS. 14A, 14B, and 14C illustrate three exemplary hypo-tube embodiments each shown penetrating through a sidewall of a lumen following a curved pathway until the distal tip of the hypotube penetrate back into the lumen wall. In these examples, the target is one or more nerves outside of the lumen at a distance "d" from the lumen outer wall. The wall thickness of the vessel varies. The wall thickness tw3 in FIG. 14C is greater than wall thickness tw2 in FIG. 14B both of which are greater than the wall thickness tw1 in FIG. 14A. It's to be appreciated that the wall thickness may be indicative of wall and artery variation between men and women, and/or adult and children. In these examples the spacing "d" indicates that the nerves 17 are spaced at a distance that does not vary or not appreciably anatomically so that the target location relative to wall for each hypotube remains constant. These examples illustrate how with a common target area the variation of a portion of the anatomy, here the thickness of the lumen used to access the treatment site, is a variable that may be addressed using different characteristics of the hypotube. No element 190 is shown for clarity but could be provided in any arrangement as described herein. In terms of tip penetration, after positioning the tip of the hypotube the tip could be on, within, or through the adjacent lumen wall or tissue structure. Depending upon the amount of anchor force desired or an action or therapeutic step to be performed or the movement of the treatment site as in the movement of the vasculature or of organs or portion of a target site due to respiration of the patient, for example. It is believed that this illustrates an exemplary case of the target anatomy (i.e., the nerves of the renal plexus) are generally spaced a distance "d" from the lumen wall. In this example, the spacing "d" approximates the same position of the nerves in each example. The hypotube radius of curvature ($r_1, r_2, r_3$) in each case varies according to the anatomical variation of the lumen wall. The radius of curvature is used to position the delivery system and the amount of anchoring force to be placed in relation to the target at or along a spacing "d."

FIG. 15A is a side view of a closed end hypotube in position for delivery of therapy to a target spaced apart from the wall with elements placed generally below the therapeutic target and without penetrating the therapeutic target.

FIG. 15B is a side view of a closed end hypotube in position for delivery of therapy to a target spaced apart from the wall with elements placed generally above or in the therapeutic target without or only slight penetration of the hypotube tip into the outer surface of the wall.

FIG. 15C is a side view of a closed end hypotube in position for delivery of therapy to a target spaced apart from the wall with elements placed generally above or in the therapeutic target with an additional length of the hypotube passed through adjacent tissue and with penetration of the hypotube tip into the outer surface of the wall.

Figure 16A:
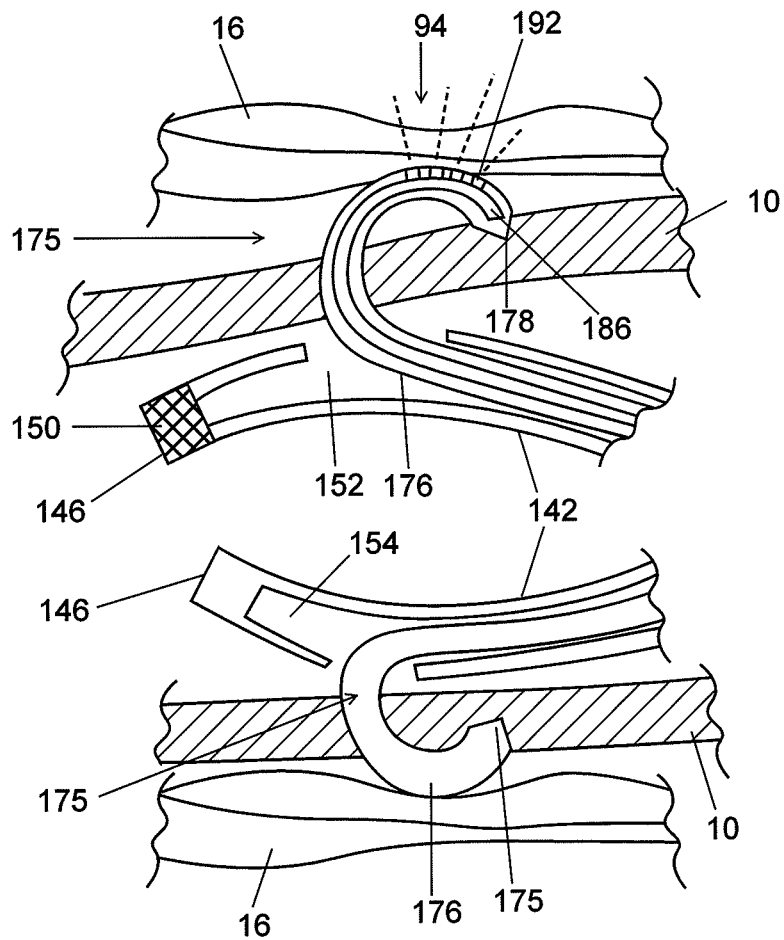
FIG. 16A is an enlarged view of the distal end of the therapy device shown in FIG. 6A modified to illustrate a mixed mode therapy to treat and anchor treatment of tissue.

FIG. 16A is an enlarged view of the distal end of the therapy device shown in FIG. 6A modified to illustrate a mixed mode therapy to treat and anchor the device. The marker bands 150 are used to denote the hollow leg 142 having the active treatment hypotube (here injection ports 192). The other hypotube is a solid used to anchor in the tissue to stabilize the device.

Figure 16B:
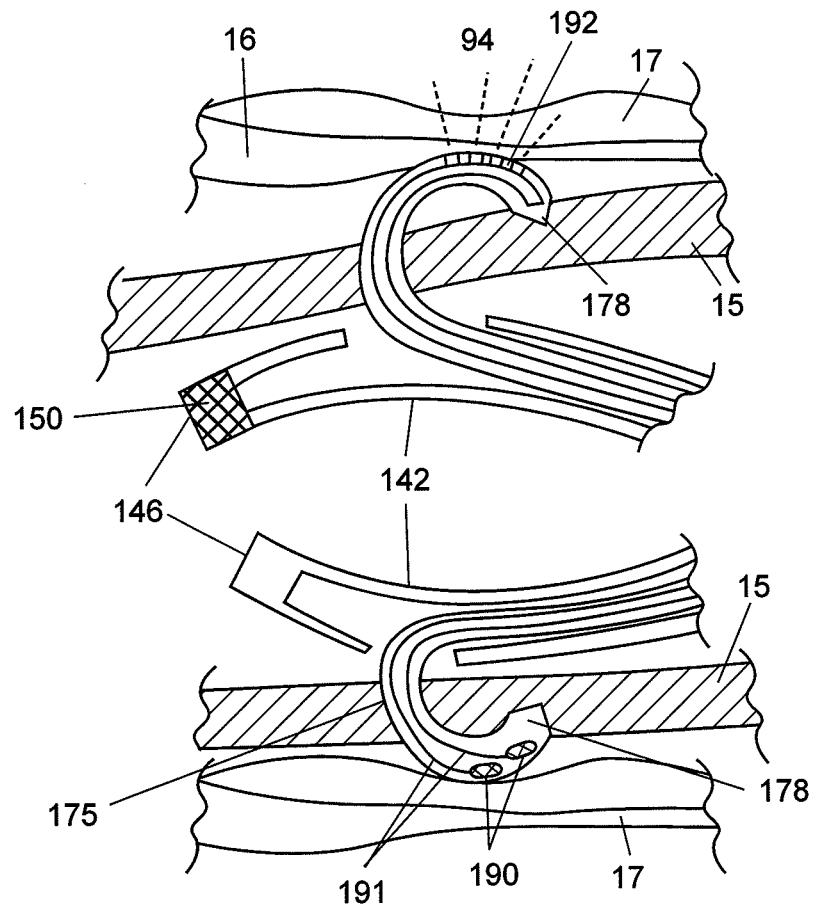
FIG. 16B is an enlarged section view of the distal end of the hollow legs of FIG. 6A showing multiple mode elements of an injection port hypotube and sensing element hypotube and a leg tip marker to denote the hollow leg having an injection port hypotube.

FIG. 16B is an enlarged section view of the distal end of the hollow legs of FIG. 6A showing multiple mode elements of an injection port hypotube and sensing element hypotube and a leg tip marker to denote the hollow leg having an injection port hypotube. Marker bands 150 can be placed on one or multiple parts of the delivery device such as the distal portion of the hollow legs, the hypotubes or other components to enable visualization during the procedure. The marker bands may be solid or split bands of platinum or other radiopaque metal, for example. As shown in FIGS. 16A and 16B marker bands are placed on the hollow leg tips 146 for those legs 142 that deliver or contain hypotubes with active elements. In this way, an active element is positioned more precisely since the tip of the leg (and thus the opening 152 and therefore exit site for the hypotube 175 is known) may be used as a proxy for targeting element placement.

Figure 18:
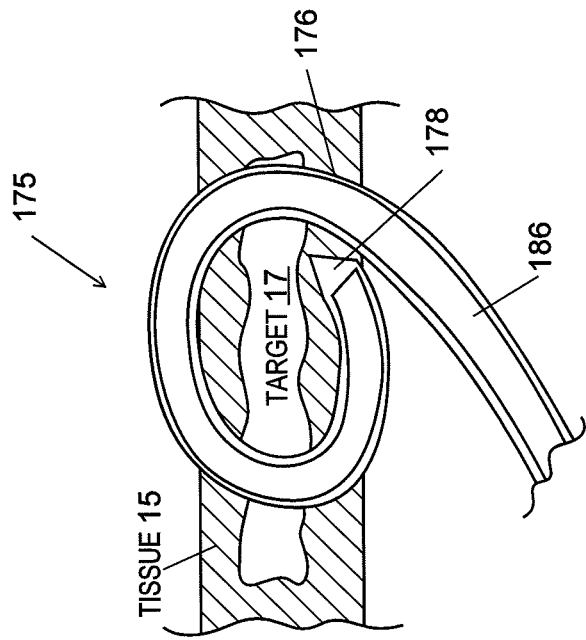
FIG. 18 is a section view of a hypotube having a radius of curvature so as to curve within the tissue and the therapeutic target.
Figure 17:
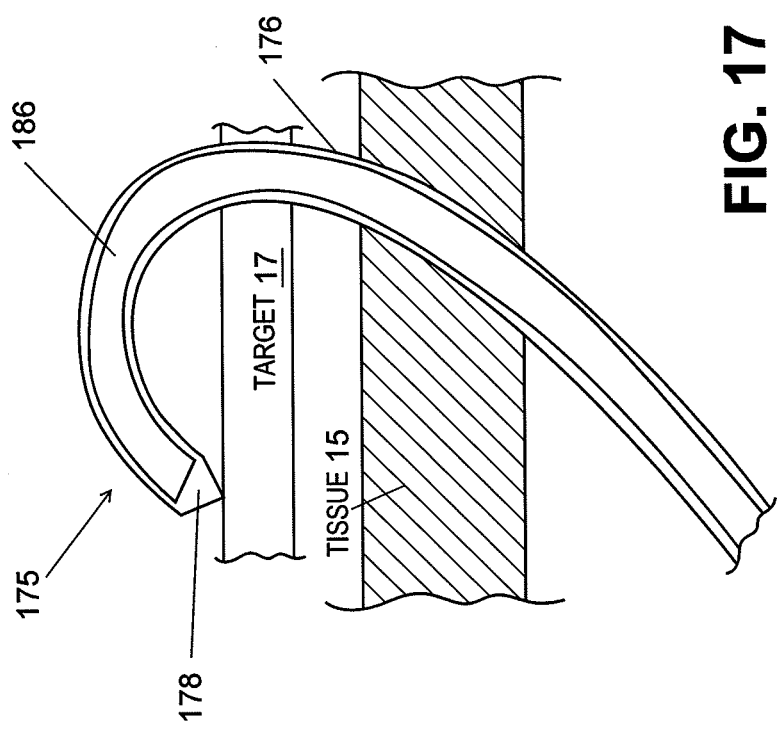
FIG. 17 is a section view of a hypotube that passes through a wall and target to anchor using the hypotube distal tip into the target.

FIG. 17 is a section view of a hypotube 175 that passes through a wall 15 and target 17 to anchor using the hypotube distal tip 178 into the target. FIG. 18 is a section view of a hypotube 175 having a radius of curvature so as to curve within the tissue 15 and the therapeutic target 17. While used primarily to illustrate radius of curvature and penetration scenarios, elements 190 have been omitted for clarity but may be provided according to any of the embodiments described herein.

In accordance with the various aspects and alternatives of the present invention, there is a hypotube delivery structure having, in use, a curved or looped path through solid or one/multiple layer(s) of tissue as best seen in FIGS. 17 and 18. Further to the illustrative hypotube deliveries of FIGS. 17 and 18, it is to be appreciated that the hypotube body 176 shape, length, and curvature along with the hypotube tip 178 (whether solid as in FIG. 12E or hollow as in FIG. 12D), hypotube fluid delivery structures, hypotube elements (in any combination) may, for example, have different shapes and be used to deliver therapy or place elements: through a membrane where the hypotube structure or device or element pierces the membrane from one side to the other an arbitrary number of times; or, on the far side of a membrane and remains on that side, after the membrane is first pierced with a device that houses the hypotube structure or device or element; or, on the far side of a membrane and pierces the membrane to enter the near side, after the membrane is first pierced with a device that houses the hypotube structure or device or element; or, on the far side of a membrane and re-pierces the membrane an arbitrary number of times, after the membrane is first pierced with a device that houses the hypotube structure or device or element; or, into solid tissue and is fully encapsulated by that tissue; or into solid tissue and re-emerges out of that tissue from the same side of entry; or into solid tissue, re-emerges out of that tissue from the same side of entry, and re-pierces the tissue an arbitrary number of times; or into solid tissue and is fully encapsulated by that tissue, after the tissue is first pierced with a device that houses the hypotube structure or device or element; or into solid tissue and re-emerges out of that tissue, after the tissue is first pierced with a device that houses the hypotube structure or device or element; or, into solid tissue, re-emerges out of that tissue, and re-pierces the tissue an arbitrary number of times, all after the tissue is first pierced with a device that houses the hypotube structure or device or element; or into porous or spongy tissue, e.g. cancellous bone; or as part of a structure that is permanently or temporarily connected to a treatment device.

Figure 19:
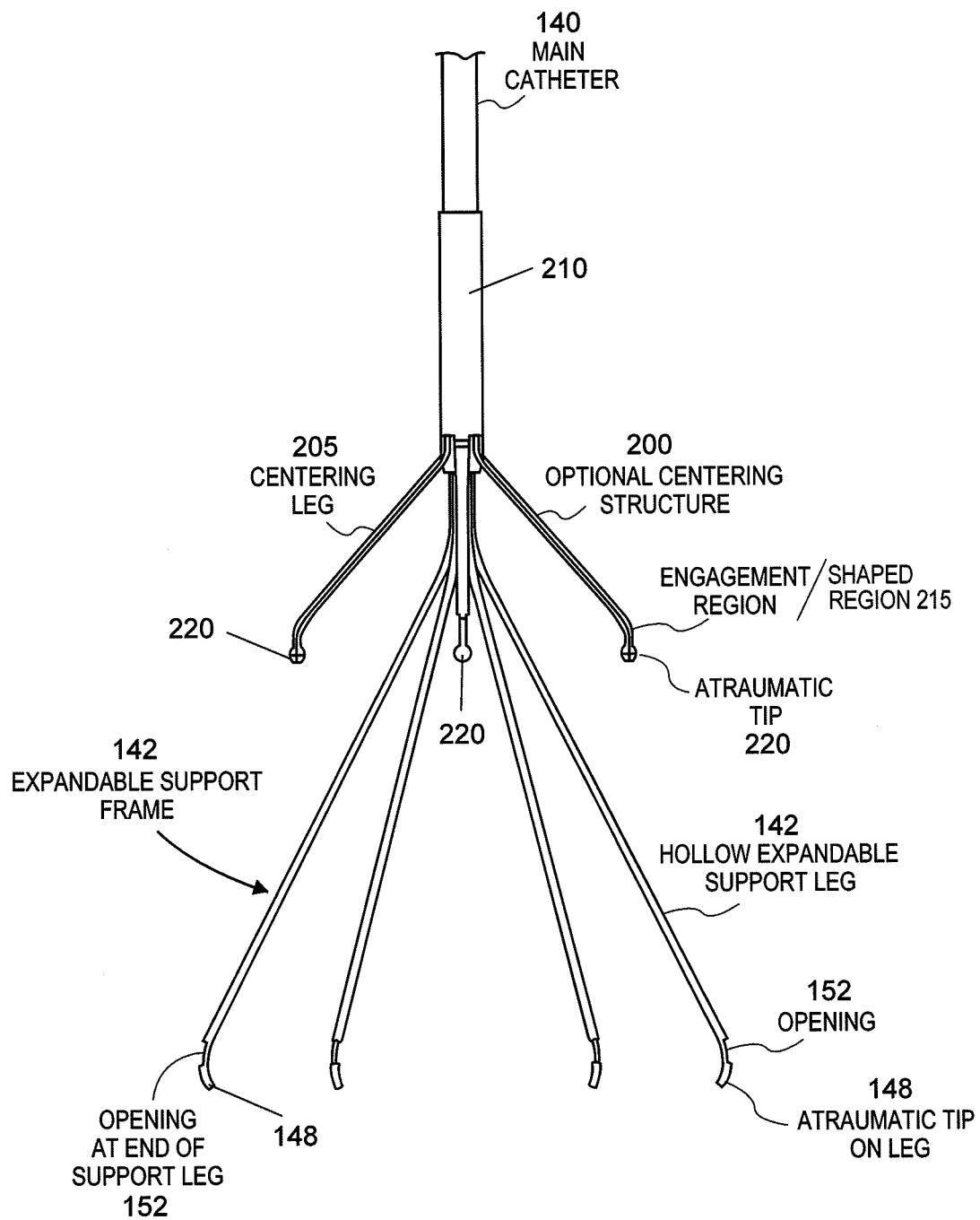
FIG. 19 is a side view of the delivery system with a four hollow leg positioning device and a centering device.

FIG. 19 is a side view of the delivery system with a four hollow leg positioning device and a centering device. The centering mechanism illustrated in FIG. 19 is positioned proximal to the positioning device provides a centering of the delivery device without obstructing blood flow. In one alternative embodiment, the centering mechanism is placed distal to the positioning device. The relative position and operation of the centering device and the position positioning device may vary depending on the specific therapeutic application. In one specific application, such as the use of the delivery device for an ablation therapy within or adjacent to a vein, the centering device may be placed distal to the delivery device in order that the centering device may open the vein in advance of the deployment of the delivery device from the delivery catheter or sheath. One exemplary venous treatment would include therapeutic uses of the devices and methods disclosed herein in relation to the pulmonary vein.

As shown in the view of FIG. 19, one alternative embodiment includes a device centering mechanism 200 that promotes the acute centering of a delivery system 100 in vivo. The centering mechanism 200 is permanently affixed to the delivery catheter 140. "Centering" refers to moving the positioning device 140 off of direct apposition with the vessel that it resides in, such that the opening of the catheter and part of the device resides within the vessel lumen rather than immediately contacting the target vessel luminal surface. The centering structure 200 includes a centering shaft 210 over and coaxial with the positioning device 140. The centering shaft 210 includes a plurality of centering legs 205. Each leg 205 has a shaped distal portion 215 and an atraumatic tip 220.

Additional aspects of the design and some features are disclosed in U.S. Pat. No. 7,056,286, titled "MEDICAL DEVICE ANCHOR AND DELIVERY SYSTEM" and in U.S. patent application Ser. No. 12/625,941, titled "MEDICAL DEVICE ANCHOR AND DELIVERY SYSTEM," now Publication No. US-2010-0076545-A1.

Additional modifications and alternative elements, delivery methods, therapeutic sites and treatments are possible, for example, as described in the following U.S. Patent Application Publications: US-2008-0213331 A1, titled "METHODS AND DEVICES FOR RENAL NERVE BLOCKING;" US-2012-0059286-A1, titled "SELF-POWERED ABLATION CATHETER FOR RENAL DENERVATION;"US-2012-0101413-A1, titled "CATHETER APPARATUSES HAVING EXPANDABLE MESH STRUCTURES FOR RENAL NEUROMODULATION AND ASSOCIATED SYSTEMS AND METHODS;"US-2012-0123406-A1, titled "SELF-EXPANDING COOLING ELECTRODE FOR RENAL NERVE ABLATION;" and US-2012-0116392-A1, titled "RF RENAL DENERVATION CATHETER WITH MULTIPLE INDEPENDENT ELECTRODES."

The embodiments shown in the figures have been generally described in the context of intravascular-based ablation of perivascular renal nerves for control of hypertension using one or more hypotube borne elements. It is understood, however, that embodiments of the disclosure have applicability in other contexts, such as one or more energy delivery or monitoring or injection elements delivered from within other vessels of the body, including other arteries, veins, and vasculature (e.g., cardiac and urinary vasculature and vessels), and other tissues of the body, including various organs. In view of the above, the methods and devices described herein may find use in a wide variety of clinical applications. Exemplary additional clinical applications include, without limitation:

Renal artery denervation
Pulmonary vein (left atrial ablation) ablation
Septal (atrial or ventricular) ablation
GI serosal surface ablation
Peptidergeric innervation (anywhere)
Migraine
Obesity
Myocardial septal hypertrophy (myocardial hypertrophy)
Sympathetic neural innnervation
Parasympathetic neural innervation
Adrenergic/Acetalcholine innervation
Vascular enervation
Tumor ablation
Stem cell delivery
Peptide delivery
Vascular occlusion In each one of the above applications the size, curvature and element or elements on one or more hypotubes are selected based on the site of treatment, location of the target site and desired treatment modality. Other additional features include, for example:

The system is comprised of a delivery sheath, the delivery catheter with integral centering mechanism, and the fluid delivery structure.

The delivery sheath is a simple tubular catheter designed, depending on the application, to be located at the intended site of ablation.

The delivery catheter is a multi-component system that provides for flushing and delivery of the appropriate therapeutic solution, gas, or current to the delivery structures (i.e., hypotube elements) located at the distal end of the positioning device A plurality of hollow leg structures 142 made of nitinol or other materials that emanate from a central proximal position located near the distal end of the delivery catheter. Each leg has a either a distal end opening or a side opening to accommodate the hypotube structures, depending on the application. For renal artery nerve ablation, a side opening is preferable. The proximal portion of the leg structures are brought together at a sleeve composed of polymer or metal that holds the preshaped hollow legs in the proper radial orientation without obstructing their lumens. Each leg is formed so that the distal end bends slightly inwards at the level of the side opening with a small extension beyond the opening that keeps the leg structure from penetrating the wall of the renal artery.

In one alternative, the collective leg structures are permanently affixed to the delivery catheter.

Radiopaque markers can be placed at the distal ends of the hollow leg 142 to provide visibility in the lumen of the renal artery.

In one aspect, a plurality of hypotube structures occupy the space within each the legs 142 of the delivery catheter. These tubular structures 175 are made of nitinol or other materials that emanate from a central proximal position such to as a cap 177. The proximal portion of the hypotube fluid delivery structures are brought together at the cap composed of polymer or metal that holds the preshaped hypotube delivery structures in the proper radial orientation without obstructing their lumens.

In another aspect, the hypotube delivery structures 175 are mechanically coupled to the delivery system 100 so that they may be extended to a variable length while maintaining connection to a proximal fluid delivery port on the delivery system (i.e., port in handle).

In still another aspect, the hypotube delivery structures may be made radiopaque by the addition of radiopaque materials at their tips, or on their outer surfaces.

The cap 177 (connected to the delivery structures 175) is shaped in a way that allows for it to be slidably moved within the legs 142 by an appropriate emotive force.

The cap is permanently affixed but slidably movable within the delivery catheter.

In still another aspect, hubs 144, 177 are fixed relative to or with the delivery catheter, they can be independently manipulated to move with respect to one another.

Various sizes and dimensions of the hypotube based delivery system are possible and may be scaled up or down depending upon the desired application for the system, the elements used and the location of the therapeutic site or target within the body. The delivery catheter is sized for use with the delivery system 100 including the positioning device 140 and the hypotubes 175. One exemplary delivery catheter has an outer diameter of 0.012" and an inner diameter of 0.078".

Additional dimensions may be considered with reference to the view of FIG. 15A. A hypotube 175 may have an outer diameter in the range of about 0.007" and an inner diameter of about 0.005". The outer diameter may range from 0.006"-0.008" inches, with an inner diameter of 0.004"-0.006". The openings 192 relate the outer diameter of the hypotube. In one exemplary embodiment, the openings are about 0.003"-0.004". Openings 192 may be in a variety of shapes and sizes such as a hole, a slot, a shaped opening (i.e., circular, oval or elliptical for example).

The openings 192 may be formed in a number of ways such as drilling, pressing, laser drilling, electric discharge machinery (e.d.m.) such as plunge e.d.m. or wire e.d.m. or other techniques selected for a desired hole, point or array of points.

The hollow leg 142 will be selected based on the size of the hypotube. The outer diameter may range from 0.016"-0.021" with an inner diameter ranging from 0.012"-0.016". The opening 152 varies depending on a number of factors. The opening 152 may be circular, oval, elliptical or other shape with a width or opening ranging from 0.008"-0.010".

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A method for performing a procedure in the body using a multiple hollow leg positioning device, comprising:
   advancing a distal most end of a catheter within a lumen of the body to a position based on a predetermined deployed position of the multiple hollow leg positioning device suited to performing the procedure;
   advancing the multiple hollow leg positioning device beyond the distal most end of the catheter to place a portion of each one of the legs of the multiple hollow leg positioning device against an inner wall of the lumen such that at least one opening in a leg in the multiple hollow leg positioning device is positioned relative to a treatment location based on a pre-determined trajectory of a hypotube disposed within a lumen of the leg;
   advancing the hypo tube through the opening in the leg until a distal most portion of the hypotube is passed completely through a wall of the lumen and an element on the distal portion of the hypotube is positioned to perform the procedure in proximity to the treatment location; and
   performing the procedure in the treatment location using the element.

2. The method of claim 1 wherein the performing the procedure step occurs outside of the lumen of the body.

3. The method of claim 1 wherein the performing the procedure step treats a neural treatment target unrelated to the lumen.

4. The method of claim 1 the performing the procedure step further comprising: delivering energy using the element.

5. The method of claim 1 further comprising: monitoring the progress or effectiveness of the performing the procedure step using an element on a hypotube provided through a lumen of another hollow leg of the multiple hollow leg positioning device.

6. The method of claim 1 further comprising continuing to advance the hypotube through the wall of the lumen to anchor the element in a position for performing the procedure.

7. The method of claim 1 wherein the lumen is a renal artery and the procedure is a denervation procedure.

8. The method of claim 1 the performing the procedure in the treatment location further comprising: delivering a fluid via the hypotube to the treatment location.

9. The method of claim 1 wherein positioned to perform a procedure in proximity to the treatment location is a position related to the therapeutic range of the energy delivered by the element.

10. The method of claim 1 wherein positioned to perform a procedure in proximity to the treatment location is a position related to the dispersion of a fluid delivered by the element.

11. A method of performing a therapy within a patient, comprising:
- positioning a delivery catheter within a blood vessel of the patient at a treatment location;
- advancing a positioning device via the delivery catheter into the blood vessel at the treatment location;
- expanding a plurality of outwardly biased hollow legs of the positioning device into engagement with an interior wall of the blood vessel in proximity to the treatment location;
- advancing hypotubes out of the hollow legs so as to pass a distal most portion of each hypotube completely through a blood vessel wall to position an element carried by the hypotube within a therapeutic range of a target in the treatment location; and
- performing an action in furtherance of the therapy using the element.

12. The method of claim 11 wherein the action in furtherance of the therapy is ablating at least a portion of the target.

13. The method of claim 12 wherein the action in furtherance of the therapy is monitoring, measuring or recording the effectiveness or progress of the ablating at least a portion of the target step.

14. The method of claim 11 wherein the target is one or more of a nerve, a ligament, a tumor, a vessel, a sphincter, an organ or a muscle.

15. The method of claim 11 wherein after the advancing hypotubes step the distal most portion of the hypotubes have exited the hollow legs via the distal most end of the hollow leg.

16. The method of claim 11 wherein after the advancing step the distal most portion of the hypotubes have exited the hollow legs via an opening in a sidewall of the hollow leg.

* * * * *